US010137212B2

(12) United States Patent
Brechbiel et al.

(10) Patent No.: US 10,137,212 B2
(45) Date of Patent: Nov. 27, 2018

(54) TETRAHYDROXAMATE CHELATORS OF ZIRCONIUM89 AND NIOBIUM90 FOR USE IN DIAGNOSTIC APPLICATIONS

(71) Applicant: The United States of America, as represented by the Secretary, Department of Health and Human Services, Washington, DC (US)

(72) Inventors: Martin W. Brechbiel, Annandale, VA (US); Francois Guerard, Washington, DC (US); Yong-Sok Lee, Fairfax Station, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 367 days.

(21) Appl. No.: 14/774,831

(22) PCT Filed: Mar. 12, 2014

(86) PCT No.: PCT/US2014/024048
§ 371 (c)(1),
(2) Date: Sep. 11, 2015

(87) PCT Pub. No.: WO2014/164988
PCT Pub. Date: Sep. 10, 2014

(65) Prior Publication Data
US 2016/0022844 A1    Jan. 28, 2016

Related U.S. Application Data

(60) Provisional application No. 61/779,016, filed on Mar. 13, 2013.

(51) Int. Cl.
*A61K 51/00* (2006.01)
*A61M 36/14* (2006.01)
*A61K 51/04* (2006.01)
*C07D 257/02* (2006.01)

(52) U.S. Cl.
CPC ......... *A61K 51/0472* (2013.01); *A61K 51/04* (2013.01); *A61K 51/044* (2013.01); *A61K 51/0482* (2013.01); *C07D 257/02* (2013.01); *A61K 51/0474* (2013.01)

(58) Field of Classification Search
None
See application file for complete search history.

(56) References Cited

U.S. PATENT DOCUMENTS

| 6,623,721 | B2 | 9/2003 | Flanagan et al. |
| 2011/0097266 | A1 | 4/2011 | Maecke et al. |
| 2012/0061325 | A1 | 3/2012 | Yokel |

FOREIGN PATENT DOCUMENTS

| WO | 2005/077967 A1 | 8/2005 | |
| WO | WO2008/124467 | * 10/2008 | ............ A61K 31/19 |
| WO | WO2011/056983 A1 | * 5/2011 | ............ A61K 51/10 |

OTHER PUBLICATIONS

Ng et al. (Inorg. Chem. 1989, 28, 2062-2066).*
Gopalan et al., "Novel Tetrahydroxamate Chelators for Actinide Complexation: Synthesis and Binding Studies," *Journal of the Chemical Society, Chemical Communications, Chemical Society*, Letchworth, GB, 1266-1268 (1992).
Hutchinson et al., "Solid Phase Extraction of Metal Ions Using Immobilised Chelating Calixarene Tetrahydroxamates," *Analytica Chimica Acta*, 291(3), 269-275 (1994).
Santos et al., "A Cyclohexane-1,2-Diyldinitrilotetraacetate Tetrahydroxamate Derivative for Actinide Complexation: Synthesis and Complexation Studies," *Journal of the Chemical Society, Dalton Transactions*, 23(1), 4398-4402 (2000).
Extended European Search Report, European Application No. 14779019.0, dated Sep. 16, 2016.
Cram, "Preorganization—From Solvents to Spherands," *Angew. Chem. Int. Ed. Engl.*, 25 (12), 1039-1057 (1986).
Deri et al., "PET imaging with $^{89}$Zr: from radiochemistry to the clinic," *Nucl. Med. Biol.*, 40 (1), 3-14 (2013).
Evans et al., "Imaging Tumor Burden in the Brain with $^{89}$Zr-Transferrin," *J. Nucl. Med.*, 54 (1), 90-95 (2013).
Fischer et al., "$^{89}$Zr, a radiometal nuclide with high potential for molecular imaging with PET: Chemistry, Applications and Remaining Challenges," *Molecules*, 18 (6), 6469-6490 (2013).
Guérard et al., "Investigation of Zr(IV) and $^{89}$Zr(IV) complexation with hydroxamates: progress towards designing a better chelator than desferrioxamine B for immuno-PET imaging," *Chem. Commun. (Camb)*, 49 (10), 1002-1004 (2013).
Holland et al., "Standardized methods for the production of high specific-activity zirconium-89," *Nucl. Med. Biol.*, 36 (7), 729-739 (2009).
International Preliminary Report on Patentability, Application No. PCT/US2014/024048, dated Sep. 15, 2015.
International Search Report, Application No. PCT/US2014/024048. dated Jul. 31, 2014.
Liu et al., "Bifunctional Chelators for Therapeutic Lanthanide Radiopharmaceuticals," *Bioconjug. Chem.*, 12 (1), 7-34 (2001).
Mathias et al., "Tumor-Selective Radiopharmaceutical Targeting via Receptor-Mediated Endocytosis of Gallium-67-Deferoxamine-Folate," *J. Nuc. Med.*, 37 (6), 1003-1008 (1996).
Nayak et al., "PET and MRI of Metastatic Peritoneal and Pulmonary Colorectal Cancer in Mice with Human Epidermal Growth Factor Receptor 1—Targeted $^{89}$ Zr-Labeled Panitumumab," *J. Nucl. Med.*, 53, 113-120 (2012).
Neu et al., "Structural Characterization of a Plutonium(IV) Siderophore Complex: Single-Crystal Structure of Pu-Desferrioxamine E," *Angew. Chem. Int. Ed. Engl.*, 39 (8), 1442-1444 (2000).

(Continued)

*Primary Examiner* — Michael G Hartley
*Assistant Examiner* — Melissa J Perreira
(74) *Attorney, Agent, or Firm* — Leydig, Voit & Mayer, Ltd.

(57) ABSTRACT

Disclosed is a compound of formula (I) or (II) in which $R^1$-$R^4$, $R^{1'}$-$R^{5'}$, $Z^1$+-$Z^4$, and $Z^{1'}$-$Z^{4'}$ are as described herein. Also disclosed are a $^{89}$Zr- or $^{90}$Nb-containing complex of a compound of formula (I) or (II) and a method for obtaining a diagnostic image, such as a positron emission tomography (PET) image.

20 Claims, 7 Drawing Sheets

(56) References Cited

OTHER PUBLICATIONS

Perk et al., p-Isothiocyanatobenzyl-desferrioxamine: a new bifunctional chelate for facile radiolabeling of monoclonal antibodies with zirconium-89 for immuno-PET imaging, *Eur. J. Nucl. Med. Mol. Imaging*, 37 (2), 250-259 (2010).

Radchenko et al., "$^{90}$Nb-a potential PET nuclide: production and labeling of monoclonal antibodies," *Radiochim. Acta*, 100 (11), 857-863 (2012).

Rossin et al., "In Vivo Chemistry for Pretargeted Tumor Imaging in Live Mice," *Angew. Chem. Int. Ed. Engl.*, 49 (19). 3375-3378 (2010).

Vosjan et al., "Conjugation and radiolabeling of monoclonal antibodies with zirconium-89 for PET imaging using the bifunctional chelate p-isothiocyanatobenzyldesferrioxamine," *Nat. Protoc.*, 5 (4) 739-743,(2010).

Written Opinion of the International Searching Authority, Application No. PCT/US2014/024048, dated Jul. 31, 2014.

Yamanaka et al., "Desferrioxamine E produced by *Streptomyces griseus* stimulates growth and development of *Streptomyces tanashiensis,*" *Microbiology*, 151 (Pt. 9), 2899-2905 (2005).

Zhou et al., "Mapping biological behaviors by application of longer-lived positron emitting ragionuclicies" *Adv. Drug Deliv. Rev.*, 65 (8), 1098-1111 (2013).

\* cited by examiner

TETRAHYDROXAMATE CHELATORS OF ZIRCONIUM89 AND NIOBIUM90 FOR USE IN DIAGNOSTIC APPLICATIONS

CROSS-REFERENCE TO RELATED APPLICATIONS

This patent application is a U.S. national phase of International Patent Application No. PCT/US2014/024048, filed March 12, which claims the benefit of U.S. Provisional Patent Application No. 61/779,016, filed Mar. 13, 2013, the disclosures of which are incorporated by reference.

STATEMENT REGARDING FEDERALLY SPONSORED RESEARCH AND DEVELOPMENT

This invention was made with Government support under Contract Number ZIA SC006353 awarded by the National Institutes of Health, National Cancer Institute. The Government has certain rights in this invention.

BACKGROUND OF THE INVENTION

Positron emitted tomography (PET) is a powerful nuclear imaging technique for the detection of various pathologies, including cancers. $^{18}$F ($T_{1/2}$=1.8 h) is currently the most commonly used β+-emitter in nuclear imaging. Other radionuclides such as $^{64}$Cu ($T_{1/2}$=12.7 h), $^{86}$Y ($T_{1/2}$=14.7 h) and $^{124}$I ($T_{1/2}$=100.2 h) have been proposed for use in PET imaging. However, there is an unmet need for additional radionuclides, especially those having half-lives that better match the blood kinetics of human patients.

BRIEF SUMMARY OF THE INVENTION

The invention provides a compound of formula (I) or (II)

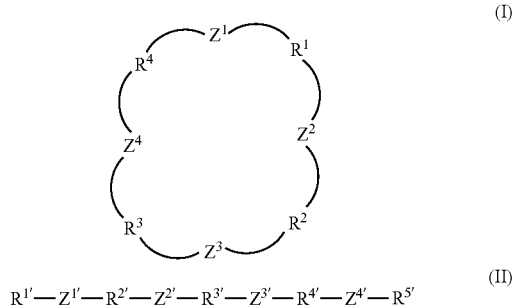

(I)

$$R^{1'}-Z^{1'}-R^{2'}-Z^{2'}-R^{3'}-Z^{3'}-R^{4'}-Z^{4'}-R^{5'}$$ (II)

in which $R^1$-$R^4$, $R^{1'}$-$R^{5'}$, $Z^1$-$Z^4$, and $Z^{1'}$-$Z^{4'}$ are as described herein.

The invention further provides a complex comprising (i) a compound of formula (I) or (II), and (ii) $^{89}$Zr or $^{90}$Nb, in which the hydrogen on the hydroxy group of each of $Z^1$-$Z^4$ and $Z^{1'}$-$Z^{4'}$ is absent, so that both oxygens of $Z^1$-$Z^4$ and $Z^{1'}$-$Z^{4'}$ are chelated to $^{89}$Zr or $^{90}$Nb.

Further provided is a method for obtaining a diagnostic image, such as a positron emission tomography (PET) image, comprising (i) administering to a subject a complex described herein in an amount effective to provide an image; and (ii) exposing the subject to an energy source, whereupon an image (e.g., PET image) of the subject is obtained.

DETAILED DESCRIPTION OF THE INVENTION

Figure 1:
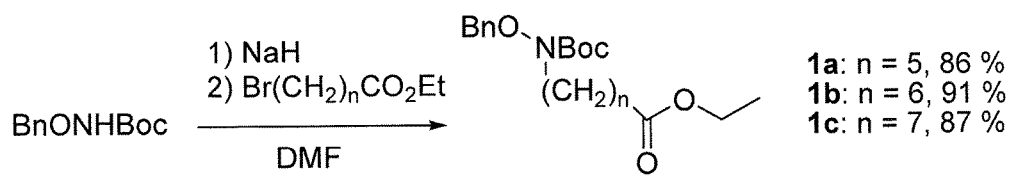
FIG. 1 is a scheme illustrating the synthesis of N-alkylated-N-Boc-O-benzylhydroxylamines 1a-c (with 1a: n=5, 1b: n=6 and 1c: n=7) in an embodiment of the invention.

The invention provides tetrahydroxamate ligands that are capable of providing a stable metal complex, such as a Zr or Nb complex, as described herein. The prearranged geometry of these chelating agents open new perspectives for the safe and efficient use of $^{89}$Zr and $^{90}$Nb in nuclear imaging. Notably, the most stable complexes described herein provide dramatically improved stabilities compared to the tris-hydroxamate desferrioxamine B (DFB). Thus, the invention provides a compound of formula (I) or (II)

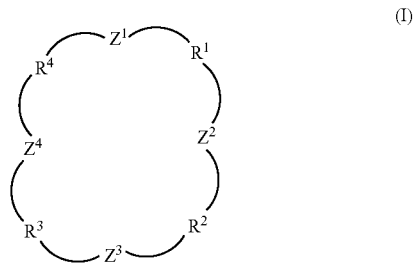

(I)

-continued

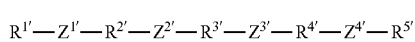
(II)

wherein $Z^1$-$Z^4$ and $Z^{1'}$-$Z^{4'}$ are the same or different and each is

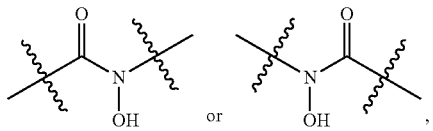 [SMILES: *C(=O)N(*)O ; *C(=O)N(*)O]

$R^1$, $R^2$, $R^3$, $R^4$, $R^{2'}$, $R^{3'}$, and $R^{4'}$, are the same or different and each is $—(CR^6R^7)_n—$ or $—(CR^8R^9)_m—X—(CR^{10}R^{11})_{m'}—$, $R^{1'}$ is $—(CR^6R^7)_nR^{12}$ or $—(CR^8R^9)_m—X—(CR^{10}R^{11})_{m'}—R^{12}$, $R^{5'}$, $R^6$, $R^7$, $R^8$, $R^9$, $R^{10}$, $R^{11}$, and $R^{12}$ are the same or different and each is selected from hydrogen, alkyl, alkenyl, cycloalkyl, alkoxy, aryl, aryloxy, heteroaryl, hydroxyalkyl, thioalkyl, thioalkoxy, thioaryl, and an amino acid-containing group, wherein each group other than hydrogen is optionally substituted, X is O, S, or $NR^3$, $R^{13}$ is hydrogen, alkyl, alkenyl, cycloalkyl, aryl, or an amino-acid containing group, wherein each group other than hydrogen is optionally substituted, n is an integer selected from 5-7, and m and m' are the same or different and each is an integer selected from 0-6, such that $4 \le (m+m') \le 6$; and wherein the compound optionally further comprises a biomolecule (i) that is covalently linked, either directly or through a linker in the compound of formula (I), to a carbon or nitrogen atom of one or more of $R^1$-$R^4$, and (ii) that is covalently linked, either directly or through a linker in the compound of formula (II), to carbon or nitrogen atom of one or more of $R^{1'}$-$R^{5'}$ or a nitrogen atom of one or both of $Z^{1'}$ or $Z^{4'}$.

The substituents $Z^1$, $Z^2$, $Z^3$, and $Z^4$ of formula (I) or $Z^{1'}$, $Z^{2'}$, $Z^{3'}$, and $Z^{4'}$ of formula (II) can be any combination of

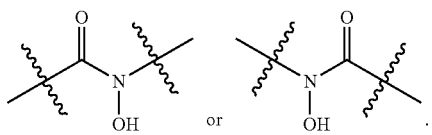 [SMILES: *C(=O)N(*)O ; *C(=O)N(*)O]

For example two substituents (e.g., $Z^1$ and $Z^2$, $Z^1$ and $Z^3$, $Z^1$ and $Z^4$, $Z^2$ and $Z^3$, $Z^2$ and $Z^4$, $Z^3$ and $Z^4$, $Z^{1'}$ and $Z^{2'}$, $Z^{1'}$ and $Z^{3'}$, $Z^{1'}$ and $Z^{4'}$, $Z^{2'}$ and $Z^{3'}$, $Z^{2'}$ and $Z^{4'}$, $Z^{3'}$ and $Z^{4'}$) can have one orientation of the hydroxamate group, and the other two Z substituents can have the opposite orientation. Alternatively, one Z group (e.g., one of $Z^1$, $Z^2$, $Z^3$, $Z^4$, $Z^{1'}$, $Z^{2'}$, $Z^{3'}$, or $Z^{4'}$) can have one orientation of the hydroxamate group, and the remaining three Z substituents can have the opposite orientation. In an embodiment, each of $Z^1$, $Z^2$, $Z^3$, and $Z^4$ or each of $Z^{1'}$, $Z^{2'}$, $Z^{3'}$, and $Z^{4'}$ is the same.

In some aspects, each of $Z^1$, $Z^2$, $Z^3$, and $Z^4$ or each of $Z^{1'}$, $Z^{2'}$, $Z^{3'}$, and $Z^{4'}$ is

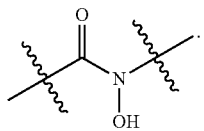 [SMILES: *C(=O)N(*)O]

With these Z groups, the core structures of formula (I) and (II) are:

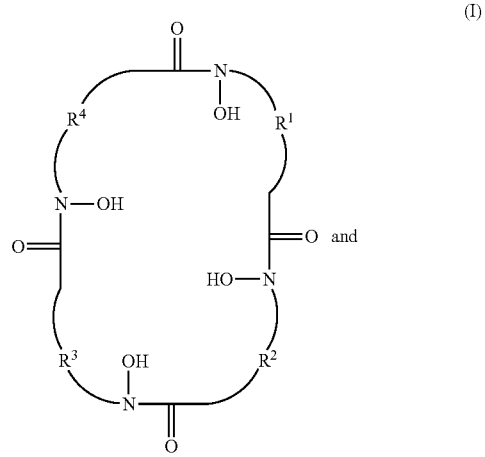

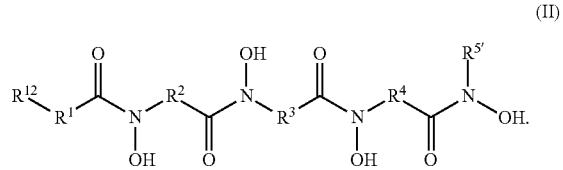

The substituents $R^1$, $R^2$, $R^3$, and $R^4$ of formula (I) and $R^{2'}$, $R^{3'}$, and $R^{4'}$ of formula (II) can be the same or different and each can be $—(CR^6R^7)_n—$ or $—(CR^8R^9)_m—X—(CR^{10}R^{11})_{m'}—$. Because $R^{1'}$ is in a terminal position in the compound of formula (II), $R^{1'}$ is $—(CR^6R^7)_nR^{12}$ or $—(CR^8R^9)_m—X—(CR^{10}R^{11})_{m'}—R^{12}$. In some embodiments, (i) each of $R^1$, $R^2$, $R^3$, and $R^4$ of formula (I) is $—(CR^6R^7)_n—$, or (ii) each of $R^{2'}$, $R^{3'}$, and $R^{4'}$ in formula (II) is $—(CR^6R^7)_n—$, and $R^{1'}$ is $—(CR^6R^7)_nR^{12}$. With these R groups, the core structures of formula (I) and (II) are:

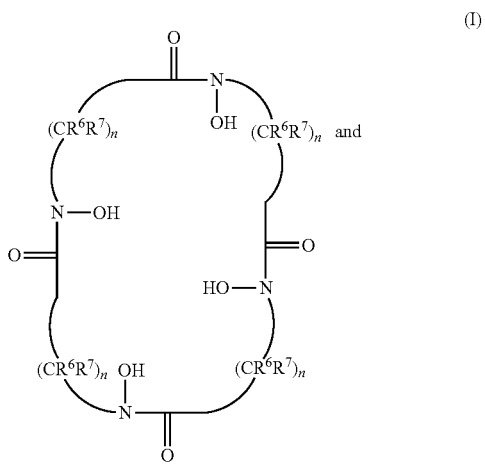

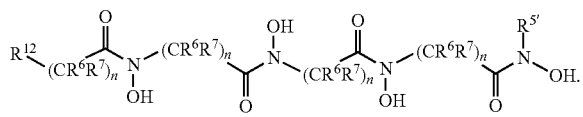

(II)

In any of the compounds described herein, $R^6$ and $R^7$ can be the same or different. In certain aspects, $R^6$ and $R^7$ can be hydrogen, optionally substituted alkyl, optionally substituted alkenyl, optionally substituted cycloalkyl, or optionally substituted aryl. In preferred embodiments, $R^6$ and $R^7$ are each hydrogen.

Any of the compounds described herein can have a structure in which at least one of $R^1$, $R^2$, $R^3$, and $R^4$ of formula (I) or at least one of $R^{2'}$, $R^{3'}$, and $R^{4'}$ of formula (II) is $-(CR^8R^9)_m-X-(CR^{10}R^{11})_{m'}-$. The substituents $R^8$, $R^9$, $R^{10}$, and $R^{11}$ can be the same or different. In certain aspects, $R^8$, $R^9$, $R^{10}$, and $R^{11}$ can be hydrogen, optionally substituted alkyl, optionally substituted alkenyl, optionally substituted cycloalkyl, or optionally substituted aryl. In preferred embodiments, $R^8$, $R^9$, $R^{10}$, and $R^{11}$ are each hydrogen.

The substituent n is an integer selected from 5-7 (i.e., 5, 6, and 7). In some aspects of the compound of formula (I) or (II), n is 7. The substituents m and m' are the same or different and each is an integer selected from 0-6 (i.e., 0, 1, 2, 3, 4, 5, and 6). The values of m and m' are selected such that $4 \leq (m+m') \leq 6$, so that a linker of 5-7 atoms is provided between each Z group. In certain aspects, (i) one of m or m' is 2, and the other is 4, (ii) one of m or m' is 1, and the other is 3, (iii) one of m or m' is 2, and the other is 3, and (iv) one of m or m' is 1, and the other is 5. In other aspects, m and m' are each 3. Each instance of n, m, and m' in a compound of formula (I) or (II) can be different.

The substituent X is O, S, or $NR^{13}$. In some embodiments, X is O. In other embodiments, X is $NR^{13}$, in which $R^{13}$ is hydrogen, optionally substituted alkyl, optionally substituted alkenyl, optionally substituted cycloalkyl, optionally substituted aryl, or an amino-acid containing group. When needed, a biomolecule can be conjugated to a compound of formula (I) or (II) through the $R^{13}$ substituent, as described herein.

In some embodiments of a compound of formula (II), $R^{5'}$ is alkyl.

In other aspects, at least one of $R^{5'}$, $R^6$, $R^7$, $R^8$, $R^9$, $R^{10}$, $R^{11}$ and $R^{12}$ is not hydrogen. For example, at least one of $R^{5'}$, $R^6$, $R^7$, $R^8$, $R^9$, $R^{10}$, $R^{11}$ and $R^{12}$ can be a substituted moiety selected from alkyl, alkenyl, cycloalkyl, alkoxy, aryl, aryloxy, heteroaryl, thioalkyl, thioalkoxy, thioaryl, and an amino acid-containing group. The substituted moiety preferably comprises at least one substituent (e.g., 1, 2, 3, 4, 5, 6, etc.) that is suitable for conjugating a biomolecule to the compound of formula (I) or (II). The substituent can be in any suitable position (e.g., 1-, 2-, 3-, 4-, 5-, or 6-position, etc.). Suitable substituents include, e.g., halo, alkyl, alkenyl, alkynyl, hydroxy, nitro, amino, alkylamino, azido, epoxidyl, vinyl sulfonyl, thiocyano, isothiocyano, alkoxy, aryloxy, aralkoxy, carboxyl, carboxyalkyl, carboxyalkyloxy, amido, alkylamido, haloalkylamido, cyclooctenyl, pyridinyl, 1,4-dihydropyridazinyl, tetrazinyl, imidazolyl, and norbornenyl. In some preferred instances, the substituent is isothiocyano (-NCS) or a haloalkylamido of the formula $-NHCOCH_2Z$, with Z being bromide or iodide.

If necessary, a linking group between the compound of formula (I) or (II) and a biomolecule can be present. Preferably, the linker is a bifunctional linker. Bifunctional linkers are known in the art (e.g., Sigma-Aldrich, St. Louis, Mo. and WO 2005/0077967). The bifunctional linker comprises any moiety that can form a chemical bond between a substituent on compound of formula (I) or (II) and at least one functional group on the biomolecule. The linker can be of any suitable charge, length and/or rigidity, but preferably the bifunctional linker is derived from a compound comprising one or more amino groups, hydroxyl, mercapto, halo groups, carboxyl groups, sulfhydryl, aryl, heteroaryl, or heterocyclyl groups prior to reaction with the compound of formula (I) or (II) and/or biomolecule.

In any of the embodiments above, the term "alkyl" means a saturated straight chain or branched non-cyclic hydrocarbon having an indicated number of carbon atoms (e.g., $C_1$-$C_{20}$, $C_1$-$C_{18}$, $C_1$-$C_{16}$, $C_1$-$C_{12}$, $C_1$-$C_{10}$, $C_1$-$C_8$, $C_1$-$C_6$, $C_1$-$C_4$, etc.). Representative saturated straight chain alkyls include methyl, ethyl, n-propyl, n-butyl, n-pentyl, n-hexyl, n-heptyl, n-octyl, n-nonyl, n-decyl, n-dodecyl, n-tetradecyl, n-hexadecyl, and n-octadecyl; while representative saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted.

In any of the embodiments above, the term "alkenyl group" means a straight chain or branched non-cyclic hydrocarbon having an indicated number of carbon atoms (e.g., $C_2$-$C_{20}$, $C_2$-$C_{18}$, $C_2$-$C_{16}$, $C_2$-$C_{14}$, $C_2$-$C_{12}$, $C_2$-$C_{10}$, etc.) and including at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, and the like. Any unsaturated group (double bond) of an alkenyl can be unconjugated or conjugated to another unsaturated group. An alkenyl group can be unsubstituted or substituted.

In any of the embodiments above, the term "alkynyl group" means a straight chain or branched non-cyclic hydrocarbon having an indicated number of carbon atoms (e.g., $C_2$-$C_{20}$, $C_2$-$C_{10}$, $C_2$-$C_6$, etc.), and including at least one carbon-carbon triple bond. Representative straight chain and branched alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. Any unsaturated group (triple bond) of an alkynyl can be unconjugated or conjugated to another unsaturated group. An alkynyl group can be unsubstituted or substituted.

In any of the embodiments above, the term "cycloalkyl," as used herein, means a cyclic alkyl moiety containing from, for example, 3 to 7 carbon atoms, preferably from 5 to 6 carbon atoms. Examples of such moieties include cyclopropyl, cyclobutyl, cyclopentyl, cyclohexyl, and the like. A cycloalkyl group can be unsubstituted or substituted.

In any of the embodiments above, the term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise $4n+2\pi$ electrons, according to Hückel's Rule, wherein n=1, 2, or 3. An aryl group can be unsubstituted or substituted.

In any of the embodiments above, the term "heteroaryl" refers to aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, pyrrolyl, thienyl, isothiazolyl, thiazolyl, isoxazolyl, and oxadiazolyl. The heteroaryl group can be unsubstituted or substituted.

In any of the embodiments above, the terms "alkoxy" and "thioalkoxy" embrace linear or branched alkyl groups that are attached to a divalent oxygen or sulfur, respectively. The alkyl group is the same as described herein. Examples of alkoxy group include methoxy, ethoxy, n-propoxy, isopropoxy, n-butoxy, sec-butoxy, isobutoxy, tert-butoxy, n-pentoxy, isopentoxy, n-hexoxy, and the like. The term "aryloxy" refers to substituents that have an aryl group attached to divalent oxygen. The aryl group is the same as described herein. Examples of such substituents include phenoxy.

In any of the embodiments above, the term "halo" refers to a halogen selected from fluorine, chlorine, bromine, and iodine, preferably fluorine, chlorine, or bromine.

In any of the embodiments above, the term "thioalkyl" denotes a substituent with an alkyl group directly attached to a divalent sulfur atom. The alkyl group is the same as described herein. Examples of such substituents include methylthio, ethylthio, and the like. Similarly, the term "thioaryl" as used herein, denotes a substituent with an aryl group directly attached to a divalent sulfur atom. The aryl group is the same as described herein.

In any of the embodiments above, the term "carboxyl" refers to the group —C(O)OH. The term "carboxyalkyl" refers to the group —RC(O)OH that is connected to the compound through the alkyl R group. The term "carboxyalkyloxy" refers to the group —ORC(O)OH, in which the R is an alkyl (e.g., $(CH_2)_n$ alkylene group, n is 1 to 12) group.

In any of the embodiments above, the term "alkylamino" refers to a secondary amine substituent with one hydrogen and one alkyl group directly attached to a trivalent nitrogen atom. In addition, the term "alkylamino" also refers to a tertiary amine substituent with two of the same or different alkyl groups directly attached to a trivalent nitrogen atom. The alkyl group is the same as described herein.

In any of the embodiments above, the term "amido" refers to the group —C(O)NH$_2$. In any of the embodiments above, the term "alkylamido" refers to substituents of the formula, —C(O)NRR' or —NRC(O)R', in which R and R' are the same or different and each is a hydrogen or alkyl group, as described herein. The term "haloalkylamido" is an alkylamido as described above, in which one or more of the alkyl groups is substituted with a halo moiety, such as, for example, chlorine, bromine, or iodine.

In any of the embodiments above, the term "amino acid-containing group" refers to a substituent that includes both a carboxyl group (C(O)OH) and an amino group (NH$_2$). Commonly, such substituents have the generic formula, —RCH(NH$_2$)CO$_2$H, in which the substituent attaches to a compound of formula (I) or (II) through the R group. Alternatively, the amino acid-containing group can attach through a nitrogen. In some embodiments, the nitrogen of the amino acid-containing group is part of X when X is NR$^{13}$. In such an instance, the remaining part of the structure of the amino-acid containing group makes up R$^{13}$. While any amino acid is to be considered (e.g., arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and trytophan) acceptable as a substituent, asparate (—CH(NH$_2$)CO$_2$H) and glutamate (—CH$_2$CH(NH$_2$)CO$_2$H) are especially preferred.

In any of the embodiments above, whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

To reach a specific tissue, a compound of formula (I) or (II) can be conjugated to a biomolecule for targeted delivery. In general, the biomolecule will be (i) covalently linked, either directly or through a linker in the compound of formula (I), to a carbon or nitrogen atom of one or more of R$^1$-R$^4$, or (ii) covalently linked, either directly or through a linker in the compound of formula (II), to carbon or nitrogen atom of one or more of $R^{1'}$-$R^{5'}$ or a nitrogen atom of one or both of $Z^{1'}$ or $Z^{4'}$. The term "biomolecule" refers to any natural or synthetic molecule that plays a role in a biological system. Biomolecules can be delivered into a subject and includes biomolecules that become localized at particular places in the subject. Examples of suitable biomolecules include, e.g., a hormone, an amino acid, a peptide, a peptidomimetic, a protein, deoxyribonucleic acid (DNA), ribonucleic acid (RNA), a lipid, albumin, an antibody, an antibody fragment, an engineered antibody fragment, a receptor molecule, a receptor binding molecule, a hapten, a pretargeting hapten, an aptamer, a nucleotide, an oligonucleotide, a polysaccharide, a bacteria, or a virus. Suitable amino acids include, e.g., arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan. Suitable peptides, peptidomimetics, and proteins comprise two or more amino acids as described herein. Suitable lipids include, e.g., glycolipids, phospholipids, sterols, prostaglandins, and leukotrienes. Suitable albumins include serum albumin (e.g., human serum albumin and bovine serum albumin). The antibody includes monoclonal and polyclonal antibodies. The antibody fragment is an active portion of any antibody and includes antigen-binding fragments (Fab) and class-defining fragments that do not bind antigen (Fc). Examples include, e.g., F(ab')2, Fab, Fab', and Fv. Suitable haptens include, e.g., aniline, o-, m-, and p-aminobenzoic acid, urushiol, quinine, hydralazine, fluorescein, biotin, digoxigenin, and dinitrophenol.

To conjugate a biomolecule to a compound of formula (I) or (II), typically a substituent will be introduced into a carbon or nitrogen atom of one or more of $R^1$-$R^4$ (i.e., through $R^{13}$), a carbon or nitrogen atom of one or more of $R^{1'}$-$R^{5'}$ (i.e., through $R^{13}$), or a nitrogen atom of one or both of $Z^{1'}$ or $Z^{4'}$. The substituent can be used directly or transformed to provide a substituent more suitable for reacting with a desired biomolecule. For instance, a substituent can be converted into a suitable leaving group by making a mesylate, tosylate, bromide, iodide, diazonium salt, and the like. In a specific example, the substituent can be a free-end nitro group, which can be reduced to an amine. The amine then can be activated with a compound, such as thionyl chloride, to form a reactive chemical group, such as an isothiocyanate. An isothiocyanate can link directly to an amino residue of a biomolecule, such as a hapten or monoclonal antibody. An aniline group can be linked to an oxidized carbohydrate on the protein and, subsequently, the linkage fixed by reduction with cyanoborohydride. An amino group also can be reacted with bromoacetyl chloride or iodoacetyl chloride to form —NHCOCH$_2$Z, with Z being bromide or iodide. This group can react with any available amine or sulfhydryl group on a biomolecule (e.g., hapten) to form a stable covalent bond.

Specific examples of a compound of formula (I) and (II) include:

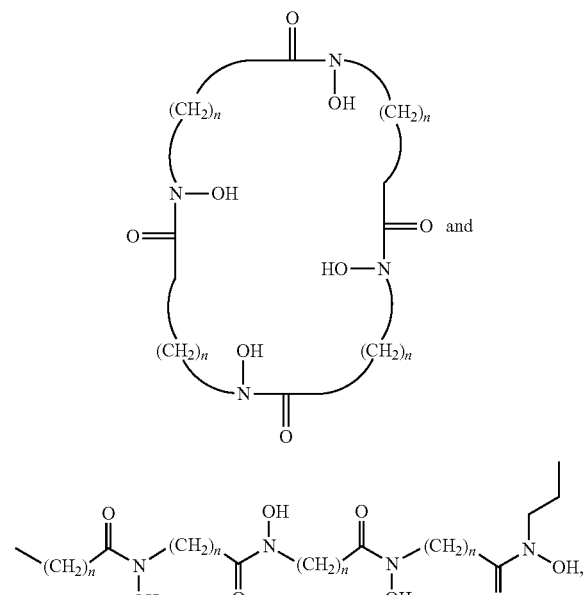

wherein each n is the same or different and is an integer from 5-7. Preferably, each n is the same and is 5, 6, or 7. In an especially preferred embodiment, each n is 7.

A specific example of a compound of formula (II) with a substituent suitable for conjugating to a biomolecule is:

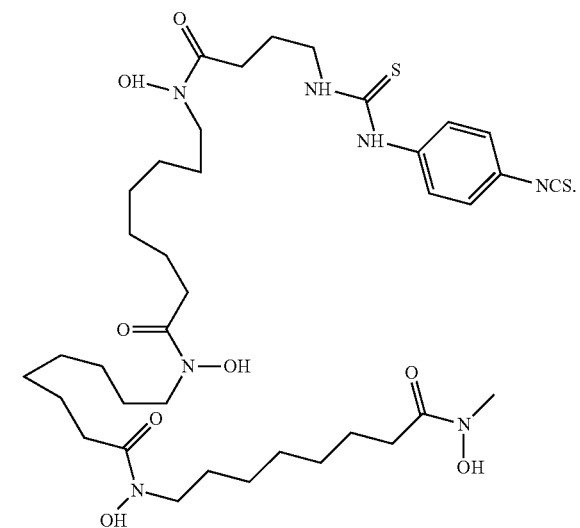

The invention further provide a complex comprising (i) a compound of formula (I) or (II), and (ii) $^{89}$Zr or $^{90}$Nb, in which the hydrogen on the hydroxy group of each of $Z^1$-$Z^4$ and $Z^{1'}$-$Z^{4'}$ is absent, so that both oxygens of $Z^1$-$Z^4$ and $Z^{1'}$-$Z^{4'}$ are chelated to $^{89}$Zr or $^{90}$Nb. In general, the compound of formula (I) or (II) will form an octahedral complex with $^{89}$Zr or $^{90}$Nb. In an embodiment, the complex can be

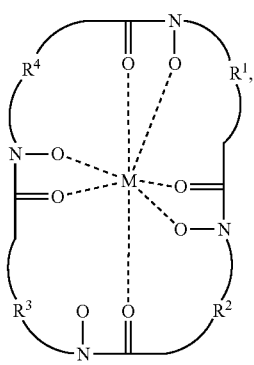

in which M is $^{89}$Zr or $^{90}$Nb. $^{89}$Zr or $^{90}$Nb can be purchased commercially, produced in a cyclotron at a PET center, prepared as described herein, or prepared by a synthesis known in the art. For example, $^{90}$Zr can be used for the production of $^{90}$Nb.

Adequate pre-organization is needed to form thermodynamically stable chelates (Cram, *Angew. Chem. Int. Ed. Engl.* 1986, 25, 1039-1057), but macrocyclic structures can also favor higher kinetic inertness of their metallic complex (Liu et al., *Bioconjugate Chem.* 2001, 12, 7-34). This factor is important when considering in vivo applications, since the metal complexes, which are highly diluted in their use, are exposed to endogenous competitive cations and natural chelators that may challenge the stability of the metal chelate. Accordingly, linkers with 5-7 atoms between the Z groups in the compounds of formula (I) and (II) were determined to be in the appropriate range to preserve the spatial orientation of the four hydroxamate ligands as observed in the X-ray structure of tetrakis(N-(hydroxyl)-N-methylacetamidato)-zirconium(IV) (Guerard et al., *Chem. Commun.* 2013, 49, 1002-1004).

The invention provides a composition comprising (a) any compound of formula (I) or (II) or any metal complex described herein; and (b) a carrier. Preferably, the carrier is a pharmaceutically acceptable carrier. The pharmaceutically acceptable carriers described herein, for example, vehicles, adjuvants, excipients, and diluents, are well-known to those skilled in the art and are readily available to the public. The choice of carrier will be determined, in part, by the particular composition and by the particular method used to administer the composition. Accordingly, there are a wide variety of suitable formulations of the pharmaceutical compositions of the present invention.

The pharmaceutical composition can be formulated for parenteral administration, such as intravenous, intraperitoneal, intramuscular, or intratumoral injection. Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injectables can be prepared in conventional forms, either as liquid solutions or suspensions, solid forms suitable for suspension in liquid prior to injection, or as emulsions. Additionally, parental administration can involve the preparation of a slow-release or sustained-release system, such that a constant dosage is maintained. Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases and the like.

Formulations suitable for oral administration can consist of (a) liquid solutions, such as an effective amount of the compound of formula (I) or (II) or a metal complex thereof dissolved in a diluent, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Suitable carriers and their formulations are further described in A. R. Gennaro, ed., *Remington: The Science and Practice of Pharmacy* (19th ed.), Mack Publishing Company, Easton, Pa. (1995).

One skilled in the art will appreciate that suitable methods of administering a composition of the present invention to a subject, e.g., a mammal such as a human, are also known. A composition comprising at least one compound of formula (I) or (II) or a metal complex thereof can be administered in any suitable manner depending on whether local or systemic treatment is desired, and on the area to be treated. Desirably, the composition is administered parenterally, most preferably by intravenous, intraperitoneal, intramuscular, or intratumoral injection. By the term "injecting," it is meant that the pharmaceutical composition is forcefully introduced into the target tissue. Although more than one route can be used to administer the pharmaceutical composition, a particular route can provide a more immediate and more effective reaction than another route. For regional delivery, the pharmaceutical composition can be administered intraarterially or intravenously, e.g., via the hepatic artery for delivery to the liver or the carotid artery for delivery to the brain.

The dose administered to a subject, particularly a human, in the context of the present invention should be an amount sufficient to allow for diagnostic imaging of the desired tissue or organ. The dose will be determined by the strength of the particular compositions employed and the condition of the subject (e.g., human), as well as the body weight of the subject (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. The dosage of the active ingredient (e.g., the radiolabeled complex) will comprise generally a low concentration of the overall composition (e.g., 1-1000 µCi/kg of body weight, 10-500 µCi/kg of body weight, or 50-250 µCi/kg of body weight). The term "Ci" refers to a Curie, which is the basic unit to describe the intensity of a radioactivity in a sample of material.

A method for obtaining a diagnostic image of a subject is provided by the present invention. When a positron-emitter (e.g., $^{89}$Zr or $^{90}$Nb) is used for metal complex of formula (I) or (II), a method for positron emission tomography (PET) imaging of a subject is provided. Such method comprises: (i) administering to the subject a complex as described herein in an amount effective to provide an image; and (ii) exposing the subject to an energy source, whereupon a PET image of the subject is obtained. PET is a non-invasive imaging method to localize the position of a target, such as a cancer metastasis. In PET, 511 keV gamma photons produced during positron annihilation decay are detected. A positron-emitting radionuclide, such as $^{89}$Zr or $^{90}$Nb, is introduced, usually by injection, and accumulates in the target tissue or organ. As it decays it emits a positron, which promptly combines with a nearby electron resulting in the simultaneous emission of two identifiable gamma rays in opposite directions. These are detected by a PET camera and give very precise indication of their origin. A PET scan can provide in vivo physiology such as metabolic detail (e.g., cellular activity) of the tumor or mass. The diagnosis is at a molecular level thereby providing detection of a tumor or mass at an early stage.

Typically one or more organs and/or target tissue will be imaged. Suitable organs and target tissues include, e.g., skin, heart, brain, esophagus, stomach, liver, gallbladder, pancreas, intestines, colon, rectum, anus, a gland, thyroid, parathyroids, kindey, ureter, bladder, urethra, lymph node, tonsil, adenoid, thymus, spleen, muscles, spinal cord, nerves, ovary, fallopian tube, uterus, vagina, mammary glands, testes, vas deferens, seminal vesicles, prostate, penis, pharynx, larynx, trachea, bronchi, lungs, diaphragm, bones, cartilage, ligament, and tendon.

For purposes of the present invention, the term "subject" preferably is directed to a mammal. Mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

Also provided is a method of obtaining a positron emission tomography (PET) image of a tissue comprising exposing the tissue to a complex as described herein in an amount effective to provide an image, and exposing the tissue to an energy source, whereupon a PET image of the tissue is obtained. The tissue to be imaged is any tissue in need thereof. Typical tissue includes an organ or a neoplastic mass (e.g., a tumor, lesion, carcinoma, sarcoma, or fibroid), as described herein. This method can be useful in imaging tissue associated with cancerous masses (e.g., tumors). The PET method can also be used to detect an antigen associated with cancer on neovasculature or an antigen in tumors like VEGF. The PET method can also be used to image inflammation of tissue or other tissues involved with targeted therapy that might require diagnosis or monitoring.

PET is a powerful imaging technique for the detection of various pathologies, including cancers. $^{89}$Zr ($T_{1/2}$=78.4 h) is particularly interesting when associated with higher molecular weight targeting agents such as cancer-targeting antibodies (Fischer et al., *Molecules* 2013, 18, 6469-6490). The half-life of $^{89}$Zr ideally matches the blood kinetics of cancer-targeting antibodies, thereby providing high sensitive imaging of tumors for several days after injection. $^{90}$Nb ($T_{1/2}$=14.6 h) allows visualizing and quantifying processes with medium and slow kinetics, such as tumor accumulation of antibodies and antibodies fragments (Radchenko et al., *Radiochimica Acta,* 2012, 100(11), 857-864).

Cancers that can be imaged with PET include neoplastic masses (e.g., tumors) associated with the oral cavity (e.g., the tongue and tissues of the mouth) and pharynx, the digestive system (e.g., the esophagus, stomach, small intestine, colon, rectum, anus, liver, gall bladder, and pancreas), the respiratory system (e.g., the larynx, lung, and bronchus), bones and joints (e.g., bony metastases), soft tissue, the skin (e.g., melanoma and squamous cell carcinoma), breast, the genital system (e.g., the uterine cervix, uterine corpus, ovary, vulva, vagina, prostate, testis, and penis), the urinary system (e.g., the urinary bladder, kidney, renal pelvis, and ureter), the eye and orbit, the brain and nervous system (e.g., glioma), and the endocrine system (e.g., thyroid). The target tissue also can be located in lymphatic or hematopoietic tissues. For example, the tumor can be associated with lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like).

Specific examples of cancers that can be imaged with the present methods include, without limitation, acute lymphoblastic leukemia, acute myeloid leukemia, adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, chronic lymphocytic, leukemia, chronic myelogenous leukemia, liver cancer, non-small cell lung cancer, small cell lung cancer, Hodgkin's disease, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous T-cell lymphoma, testicular cancer, malignant thymoma, thyroid cancer, gestational trophoblastic tumor, urethral cancer, uterine sarcoma, vaginal cancer, vulvar cancer, and Wilms' tumor.

The cancers that can be imaged by the methods of the present invention include, without limitation, brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

The following examples further illustrate the invention but, of course, should not be construed as in any way limiting its scope.

EXAMPLES

All reagents and solvents were obtained commercially and used without further purification unless otherwise noted. N-Boc-O-benzylhydroxylamine was prepared as previously reported. $^1$H NMR and $^{13}$C NMR spectra were recorded on a Bruker Advance 300 MHz instrument, and chemical shifts are reported in ppm on the δ scale relative to TMS. Electrospray ionization-mass spectra (ESI-MS) were acquired using an Agilent LC/MS system equipped with a multimode ion. Elemental analyses were performed by Galbraith Lab. Inc. (Knoxville, Tenn.) using combustion analysis methods for C, H, and N and inductively coupled plasma-atomic emission spectroscopy (ICP-OES) method for Zr. FT-IR spectra were recorded on a MIRACLE™ Single Reflection ATR spectrometer (PIKE technologies, Madison, Wis.).

Example 1

This example demonstrates the synthesis of N-alkylated-N-Boc-O-benzylhydroxylamines 1a-c (FIG. 1) in an embodiment of the invention.

N-Boc-O-benzylhydroxylamine (5.00 g, 22.4 mmol) under nitrogen atmosphere was dissolved in dry DMF (100 mL) and cooled in an ice bath. 60% sodium hydride (887 mg, 22.2 mmol) was added and the mixture was stirred until end of hydrogen evolution (30 min). Ethyl-6-bromohexanoate (6.19 g, 28 mmol) was added and the mixture was heated for 14 h at 65° C. The DMF was then evaporated in vacuo, the residue was dissolved in AcOEt and washed twice with water. After drying the organic layer with MgSO$_4$, the oil obtained after filtration and concentration was purified by flash chromatography using hexane/acetone (9/1), affording 1a as a colorless oil (7.04 g, 86%). $^1$H NMR (CDCl$_3$, 300 MHz, ppm): δ 1.24 (t, 3H, J=7.2 Hz), 1.31 (m, 2H), 1.50 (s, 9H), 1.61 (m, 4H), 2.28 (t, 2H, J=7.5 Hz), 3.40 (t, 2H, J=7.2 Hz), 4.11 (q, 2H, J=7.2 Hz), 4.82 (s, 2H), 7.36 (m, 5H). $^{13}$C NMR (CDCl$_3$, 75 MHz, ppm): δ 14.4, 24.8, 26.5, 26.9, 28.5, 34.4, 49.6, 60.4, 77.1, 81.4, 128.6 (2), 129.5, 135.9, 156.8, 173.8. ESI-MS: m/z=266.2 [M+H]$^+$.

The same alkylation procedure using ethyl-7-bromoheptanoate provided 1b as a colorless oil (91%). $^1$H NMR (CDCl$_3$, 300 MHz, ppm): δ 1.24 (t, 3H, J=7.2), 1.31 (m, 4H), 1.50 (s, 9H), 1.60 (m, 4H), 2.27 (t, 2H, J=7.5 Hz), 3.40 (t, 2H, J=6.9 Hz), 4.11 (q, 2H, J=6.9H), 4.82 (s, 2H), 7.33 (m, 5H). $^{13}$C NMR (CDCl$_3$, 75 MHz, ppm): (δ 14.3, 24.9, 26.5, 26.9, 28.4, 28.8, 34.3, 49.6, 60.2, 76.9, 81.1, 128.4, 128.5, 129.4, 135.8, 156.6, 173.7. ESI-MS: m/z=402.2 [M+Na]$^+$.

The same alkylation procedure using ethyl-8-bromooctanoate provided 1c as a colorless oil (87%). $^1$H NMR (CDCl$_3$, 300 MHz, ppm): δ 1.24 (t, 3H, J=7.2 Hz), 1.30 (m, 6H), 1.50 (s, 9H), 1.61 (m, 4H), 2.27 (t, 2H, J=7.2 Hz), 3.39 (t, 2H, J=7.2 Hz), 4.11 (q, 2H, J=7.2 Hz), 4.82 (s, 2H), 7.33 (m, 5H). $^{13}$C NMR (CDCl$_3$, 75 MHz, ppm): δ 14.3, 24.9, 26.6, 27.1, 28.4, 29.0, 29.1, 34.4, 49.6, 60.2, 76.9, 81.1, 128.4, 128.5, 129.4, 135.8, 156.7, 173.8. ESI-MS: m/z=416.2 [M+Na]$^+$, 294.2 [M-Boc+2H]$^+$.

Example 2

Figure 2:
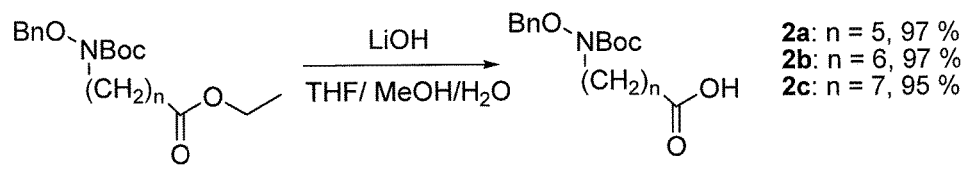
FIG. 2 is a scheme illustrating the synthesis of carboxylic acid building blocks 2a-c in an embodiment of the invention.

This example demonstrates the synthesis of carboxylic acid building blocks 2a-c (FIG. 2) in an embodiment of the invention.

Compound 1a (2.215 g, 6.06 mmol) prepared in Example 1 was dissolved in 18 ml THF+6 mL MeOH, and 6 mL of 2M LiOH (12 mmol) was added dropwise, and the mixture was stirred for 4 h at room temperature. After removal of the solvents in vacuo, the residue was dissolved in Et$_2$O and washed with 1M HCl. The organic layer was dried over MgSO$_4$, filtered, and evaporated to afford 2a as a colorless oil (1.93 g, 97%). $^1$H NMR (CDCl$_3$, 300 MHz, ppm): δ 1.33 (m, 2H), 1.50 (s, 9H), 1.62 (m, 4H), 2.34 (t, 2H, J=7.2 Hz), 3.41 (t, 2H, J=7.2 Hz), 4.82 (s, 2H), 7.35 (m, 5H). $^{13}$C NMR (CDCl$_3$, 75 MHz, ppm): δ 24.5, 26.4, 26.9, 28.5, 34.0, 49.5, 77.1, 81.5, 128.6, 128.7, 129.6, 135.8, 156.8, 179.6. ESI-MS: m/z=360.1 [M+Na]$^+$, 238.1 [M-Boc+2H]$^+$.

The same procedure starting with compound 1b afforded 2b as a colorless oil (97%). $^1$H NMR (CDCl$_3$, 300 MHz, ppm): δ 1.32 (m, 4H), 1.50 (s, 9H), 1.60 (m, 4H), 2.33 (t, 2H, J=7.5 Hz), 3.40 (t, 2H, J=7.2 Hz), 4.82 (s, 2H), 7.35 (m, 5H). $^{13}$C NMR (CDCl$_3$, 75 MHz, ppm): δ 24.7, 26.6, 27.0, 28.5, 28.9, 34.1, 49.7, 77.1, 81.4, 128.6, 128.7, 129.6, 135.9, 156.8, 179.8. ESI-MS: m/z=374.2 [M+Na]$^+$.

The same procedure starting with compound 1c afforded 2c as a colorless oil (95%). $^1$H NMR (CDCl$_3$, 300 MHz, ppm): δ 1.34 (m, 6H), 1.50 (s, 9H), 1.60 (m, 4H), 2.33 (t, 2H, J=7.5 Hz), 3.40 (t, 2H, J=7.2 Hz), 4.82 (s, 2H), 7.35 (m, 5H). $^{13}$C NMR (CDCl$_3$, 75 MHz, ppm): δ 24.9, 26.9, 27.3, 28.9, 29.2, 29.3, 34.4, 49.9, 77.9, 81.5, 128.7, 128.8, 129.7, 136.0, 157.0, 180.3. ESI-MS: m/z=388.2 [M+Na]$^+$.

Example 3

Figure 3:
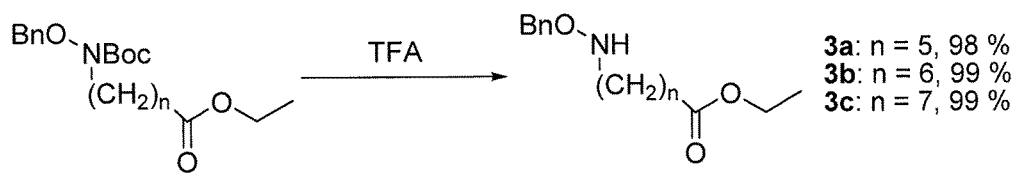
FIG. 3 is a scheme illustrating the synthesis of O-benzylhydroxylamine building blocks 3a-c in an embodiment of the invention.

This example demonstrates the synthesis of O-benzylhydroxylamine building blocks 3a-c (FIG. 3) in an embodiment of the invention.

To compound 1a (2.544 g, 6.96 mmol) cooled in an ice bath, was added dropwise trifluoroacetic acid (3.22 mL, 41.8 mmol). The mixture was stirred at room temperature for 3 h. CH$_2$Cl$_2$ (50 mL) and water (50 mL) were then added and the solution was raised to pH 10-11 by addition of solid Na$_2$CO$_3$. After drying the organic layer over MgSO$_4$ and filtration, the solution was concentrated in vacuo to afford 3a as a colorless liquid (1.81 g, 98%). NMR (CDCl$_3$, 300 MHz, ppm): b 1.30 (t, 3H, J=6.6 Hz), 1.37 (m, 2H), 1.53 (m, 2H), 1.63 (m, 2H), 2.29 (t, 2H, J=7.5 Hz), 2.93 (t, 2H, J=7.2 Hz), 4.12 (q, 2H, J=7.2 Hz), 4.70 (s, 2H), 5.54 (s, 1H), 7.34 (m, 5H). $^{13}$C NMR (CDCl$_3$, 75 MHz, ppm): 14.4, 25.0, 26.9, 27.2, 34.4, 52.1, 60.4, 76.4, 128.0, 128.6 (2), 138.2, 173.9. ESI-MS: m/z=266.2 [M+H]$^+$.

The same procedure starting with compound 1b afforded 3b as a colorless liquid (99%). $^1$H NMR (CDCl$_3$, 300 MHz, ppm): δ 1.24 (t, 3H, J=7.2 Hz), 1.32 (m, 4H), 1.51 (m, 2H), 1.62 (m, 2H), 2.28 (t, 2H, J=7.2 Hz), 2.91 (t, 2H, J=6.9 Hz), 4.11 (q, 2H, J=7.2 Hz), 4.69 (s, 2H), 5.53 (s, 1H) 7.31 (m, 5H). $^{13}$C NMR (CDCl$_3$, 75 MHz, ppm): δ 14.4, 25.0, 26.9, 27.3, 29.1, 34.4, 52.2, 60.3, 76.3, 127.8, 128.4, 138.1, 173.8. ESI-MS: m/z=280.1 [M+H]$^+$; 302.1 [M+Na]$^+$.

The same procedure starting with compound 1c afforded 3c as a colorless liquid (99%). $^1$H NMR (CDCl$_3$, 300 MHz, ppm): δ 1.25 (t, 3H, J=7.2 Hz), 1.31 (m, 6H), 1.48 (m, 2H), 1.61 (m, 2H), 2.28 (t, 2H, J=7.5 Hz), 2.92 (t, 2H, J=7.2 Hz), 4.12 (q, 2H, J=7.2 Hz), 4.70 (s, 2H), 5.53 (s, 1H), 7.35 (m, 5H). $^{13}$C NMR (CDCl$_3$, 75 MHz, ppm): δ 14.5, 25.1, 27.2, 27.5, 29.2, 29.3, 34.5, 52.3, 60.4, 76.4, 128.0, 128.5, 128.6, 138.2, 174.0. ESI-MS: m/z=294.2 [M+H]$^+$.

Example 4

Figure 4:
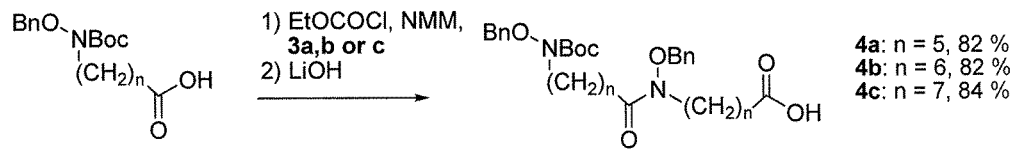
FIG. 4 is a scheme illustrating the synthesis of O-benzyl monohydroxamates 4a-c in an embodiment of the invention (NMM is N-methylmorpholine; TFA is trifluoroacetic acid).

This example demonstrates the synthesis of O-benzyl monohydroxamates 4a-c (FIG. 4) in an embodiment of the invention.

To compound 2a (4.213 g, 12.5 mmol) dissolved in dry Et$_2$O (100 mL) and cooled in an ice bath, was slowly added ethylchloroformate (1.43 mL, 15 mmol), followed by N-methylmorpholine (2.06 mL, 18.8 mol). The mixture was stirred for 15 min and the precipitate was removed by filtration. The filtrate was then poured onto compound 3a and the mixture stirred at rt for 4 h. The solution was then washed twice with 1N HCl and twice with 1M Na$_2$CO$_3$. After drying over MgSO$_4$ and concentration in vacuo, the oily residue was purified by flash chromatography using hexane/acetone (9/1) to afford the ester intermediate as a colorless oil (5.763 g, 83%). It was treated with LiOH with the hydrolysis procedure described above to afford 4a as a colorless oil (5.70 g, 82% from 2a). $^1$H NMR (CDCl$_3$, 300 MHz, ppm): δ 1.30 (m, 4H), 1.49 (s, 9H), 1.62 (m, 8H), 2.35 (m, 4H), 3.41 (t, 2H, J=6.9 Hz), 3.64 (t, 2H, J=6.9 Hz), 4.77 (s, 2H), 4.81 (s, 2H), 7.36 (m, 10H). $^{13}$C NMR (CDCl$_3$, 75 MHz, ppm): δ 24.5, 26.3, 26.7, 27.0, 28.5, 31.1, 32.4, 34.0, 76.4, 77.0, 81.4, 128.5, 128.6, 128.9, 129.1, 129.3, 129.5, 134.7, 135.7, 156.8, 178.6. ESI-MS: m/z=579.3 [M+Na]$^+$; 457.3 [M-Boc+2H]$^+$.

The same condensation procedure between 2b and 3b, followed by ester hydrolysis afforded compound 4b as a colorless oil (82%). $^1$H NMR (CDCl$_3$, 300 MHz, ppm): δ 1.30 (m, 8H), 1.49 (s, 9H), 1.60 (m, 8H), 2.32 (m, 4H), 3.39 (t, 2H, J=7.2 Hz), 3.61 (t, 2H, J=6.9 Hz), 4.79 (s, 2H), 4.81 (s, 2H), 7.34 (m, 10H). $^{13}$C NMR (CDCl$_3$, 75 MHz, ppm): δ 24.7, 25.7, 26.5, 26.7, 26.8, 27.11, 28.5, 28.8, 29.3, 32.5, 34.1, 49.7, 53.6, 76.4, 77.0, 81.3, 128.5, 128.6, 128.9, 129.1, 129.2, 129.5, 134.7, 135.8, 156.8, 179.1. ESI-MS: m/z=607.3 [M+Na]$^+$; 485.3 [M-Boc+2H]$^+$.

The same condensation procedure between 2c and 3c, followed by ester hydrolysis afforded compound 4c as a colorless oil (82%). $^1$H NMR (CDCl$_3$, 300 MHz, ppm): δ 1.30 (m, 12H), 1.49 (s, 9H), 1.60 (m, 8H), 2.34 (m, 4H), 3.39 (t, 2H, J=7.2 Hz), 3.62 (t, 2H, J=6.9 Hz), 4.79 (s, 2H), 4.81 (s, 2H), 7.34 (m, 10H). $^{13}$C NMR (CDCl$_3$, 75 MHz, ppm): δ 24.8, 26.7, 26.8, 27.0, 27.2, 28.5, 29.0, 29.1, 29.3, 29.5, 32.6, 34.1, 49.8, 76.5, 77.1, 81.4, 128.6, 128.7, 128.9, 129.1, 129.3, 129.6, 134.1, 135.9, 156.8, 178.9. ESI-MS: m/z=635.3 [M+Na]$^+$; 513.3 [M-Boc+2H]$^+$.

Example 5

Figure 5:
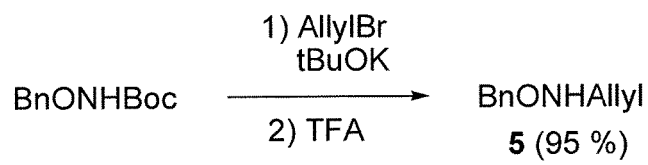
FIG. 5 is a scheme illustrating the synthesis of N-allyl-O-benzylhydroxylamine 5 in an embodiment of the invention (NMM is N-methylmorpholine; TFA is trifluoroacetic acid).

This example demonstrates the synthesis of N-allyl-O-benzylhydroxylamine 5 (FIG. 5) in an embodiment of the invention.

N-Boc-O-benzylhydroxylamine (2.203 g, 9.87 mmol) was melted by heating at 60° C. and, after cooling, allyl bromide (1.7 mL, 19.74 mmol) was added, followed by potassium tert-butoxide (1.383 g, 12.34 mmol). After heating at 60° C. for 4 h, the mixture was cooled to rt, water was added and the product was extracted by CH$_2$Cl$_2$, dried over MgSO$_4$, filtered and concentrated in vacuo resulting in an oily residue. Purification by flash chromatography using hexane/acetone (95/5) afforded a colorless oil (2.554 g). To this oil was added TFA (4.53 mL, 59.2 mmol) and the mixture was stirred at rt for 4 h. It was then diluted with CH$_2$Cl$_2$ (150 mL) and water (75 mL). Solid Na$_2$CO$_3$ was added until pH=10-11. The organic layer was dried over MgSO$_4$, filtered and concentrated in vacuo to afford compound 5 as a colorless liquid (2.09 g, 95%). $^1$H NMR (CDCl$_3$, 300 MHz, ppm): δ 3.55 (d, 2H, J=6.3 Hz), 4.72 (s, 2H), 5.20 (m, 2H), 5.55 (s, 1H), 5.94 (m, 1H), 7.35 (m, 5H). $^{13}$C NMR (CDCl$_3$, 75 MHz): δ 55.2, 76.4, 118.1, 128.0, 128.6 (2), 134.5, 138.1. ESI-MS: m/z=164.0 [M+H]$^+$.

Example 6

Figure 6:
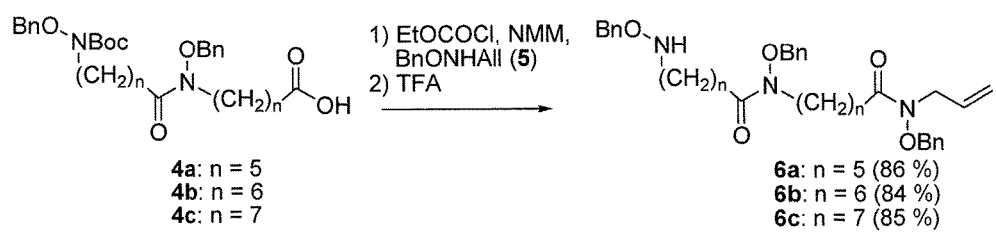
FIG. 6 is a scheme illustrating the synthesis of O-benzylated dihydroxamates 6a-c in an embodiment of the invention (NMM is N-methylmorpholine; TFA is trifluoroacetic acid).

This example demonstrates the synthesis of O-benzylated dihydroxamates 6a-c (FIG. 6) in an embodiment of the invention.

The condensation of 4a with compound 5 was performed following the procedure described above. The oily residue was purified by flash chromatography with hexane/acetone (4/1) to afford a colorless oil. The Boc protection was then removed in the presence of TFA as described above to form 6a as a colorless oil (3.45 g, 86%). $^1$H NMR (CDCl$_3$, 300 MHz, ppm): δ 1.33 (m, 4H), 1.53 (m, 2H), 1.60 (m, 6H), 2.38 (m, 4H), 2.91 (t, 2H, J=7.2 Hz), 3.61 (t, 2H, J=6.9 Hz), 4.23 (d, 2H, J=5.7 Hz), 4.69 (s, 2H), 4.78 (s, 2H), 4.82 (s, 2H), 5.21 (m, 2H), 5.51 (s, 1H), 5.84 (m, 1H), 7.36 (m, 15H). $^{13}$C NMR (CDCl$_3$, 75 MHz, ppm): δ 24.4, 24.7, 26.8, 27.0, 27.2, 27.4, 32.4, 52.2, 76.4, 76.5, 77.0, 118.5, 127.9, 128.5, 128.6, 128.8, 128.9, 129.1, 129.3, 129.4, 132.6, 134.8, 138.2, 140.3. ESI-MS: m/z=602.4 [M+H]$^+$; 624.3 [M+Na]$^+$.

The same condensation reaction between 4b and 5 followed by Boc removal afforded 6b as a colorless oil (84%). $^1$H NMR (CDCl$_3$, 300 MHz, ppm): δ 1.30 (m, 8H), 1.47 (m, 2H), 1.61 (m, 6H), 2.37 (m, 4H), 2.93 (t, 2H, J=6.9 Hz), 3.60 (t, 2H, J=7.2 Hz), 4.23 (d, 2H, J=6.0 Hz), 4.69 (s, 2H), 4.78 (s, 2H), 4.82 (s, 2H), 5.22 (m, 2H), 5.52 (s, 1H), 5.84 (m, 1H), 7.36 (m, 15H). $^{13}$C NMR (CDCl$_3$, 75 MHz, ppm): δ 24.5, 24.7, 26.8, 27.0, 27.2, 27.4, 29.2, 29.5, 32.5, 52.3, 76.3, 76.4, 77.0, 118.4, 127.9, 128.5 (2), 128.9, 129.0, 129.1, 129.2, 129.3, 132.6, 134.7, 134.8, 138.2, 174.9. ESI-MS: m/z=630.4 [M+H]$^+$.

The same condensation reaction between 4c and 5 followed by Boc removal afforded 6c as a colorless oil (85%). $^1$H NMR (CDCl$_3$, 300 MHz, ppm): δ 1.29 (m, 12H), 1.47 (m, 2H), 1.58 (m, 6H), 2.37 (m, 4H), 2.91 (t, 2H, J=6.9 Hz), 3.60 (t, 2H, J=6.9 Hz), 4.24 (d, 2H, J=5.7 Hz), 4.70 (s, 2H), 4.80 (s, 2H), 4.83 (s, 2H), 5.22 (m, 2H), 5.53 (s, 1H), 5.86 (m, 1H), 7.36 (m, 15H). $^{13}$C NMR (CDCl$_3$, 75 MHz, ppm): δ 24.6, 24.7, 26.8, 27.1, 27.2, 27.5, 29.2, 29.4, 29.5, 32.5, 52.3, 76.3, 76.4, 77.0, 77.4, 118.4, 127.9, 128.5 (2), 128.8, 128.9, 129.0, 129.1, 129.2, 129.3, 132.6, 134.8, 138.2. ESI-MS: m/z=658.4 [M+H]$^+$; 680.4 [M+Na]$^+$.

Example 7

Figure 7:
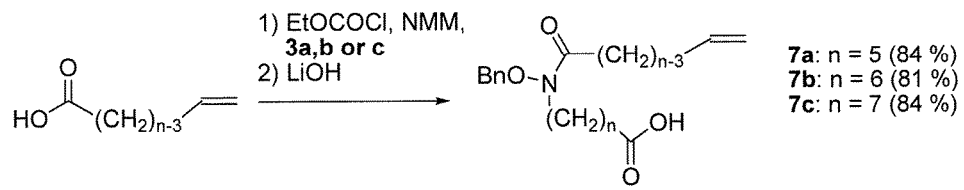
FIG. 7 is a scheme illustrating the synthesis of O-benzyl monohydroxamates 1a-c in an embodiment of the invention.

This example demonstrates the synthesis of O-benzyl monohydroxamates 7a-c (FIG. 7) in an embodiment of the invention.

Condensation of 4-pentenoic acid with 3a using the method described above afforded the ester intermediate as a colorless oil after purification by flash chromatography with hexane/acetone (95/5). Hydrolysis of the ester using the procedure described above afforded 7a as a colorless oil (84%). $^1$H NMR (CDCl$_3$, 300 MHz, ppm): δ 1.36 (m, 2H), 1.64 (m, 4H), 2.34 (m, 4H), 2.50 (m, 2H), 3.64 (m, 2H), 4.80 (s, 2H), 4.99 (m, 2H), 5.80 (m, 1H), 7.40 (m, 5H). $^{13}$C NMR (CDCl$_3$, 75 MHz, ppm): δ 24.5, 26.4, 26.7, 28.8, 31.8, 34.0, 45.4, 76.6, 115.3, 128.9, 129.2, 129.3, 134.7, 137.6, 179.2. ESI-MS: m/z=320.2 [M+H]$^+$; 342.2 [M+Na]$^+$.

Condensation of 5-hexenoic acid with 3b using the method described above followed by hydrolysis afforded 7b as a colorless oil (81%). $^1$H NMR (CDCl$_3$, 300 MHz, ppm): δ 1.33 (m, 4H), 1.60 (m, 6H), 2.06 (m, 2H), 2.36 (m, 4H), 3.63 (m, 2H), 4.80 (s, 2H), 4.95 (m, 2H), 5.78 (m, 1H), 7.41 (m, 5H). $^{13}$C NMR (CDCl$_3$, 75 MHz, ppm): δ 23.9, 24.7, 26.5, 26.9, 28.8, 31.8, 33.5, 34.1, 45.6, 76.5, 115.3, 128.9, 129.1, 129.3, 134.7, 138.3, 175.0, 179.4. ESI-MS: m/z=348.2 [M+H]$^+$; 370.2 [M+Na]$^+$.

Condensation of 6-heptenoic acid with 3c using the method described above followed by hydrolysis afforded 7c as a colorless oil (81%). $^1$H NMR (CDCl$_3$, 300 MHz, ppm): δ 1.31 (m, 8H), 1.61 (m, 6H), 2.04 (m, 2H), 2.35 (m, 4H), 3.62 (m, 2H), 4.80 (s, 2H), 4.95 (m, 2H), 5.78 (m, 1H), 7.37 (m, 5H). $^{13}$C NMR (CDCl$_3$, 75 MHz, ppm): δ 24.4, 24.8, 26.7, 27.0, 28.8, 29.0, 29.1, 32.4, 34.1, 76.5, 114.7, 128.9, 129.1, 129.3, 134.8, 138.8, 179.3. ESI-MS: m/z=376.3 [M+H]$^+$; 398.3 [M+Na]$^+$.

Example 8

Figure 8:
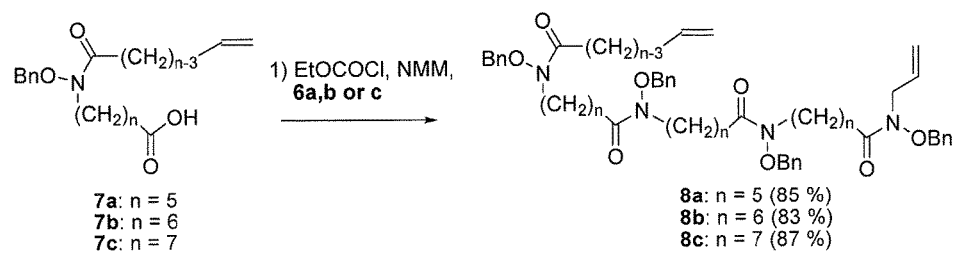
FIG. 8 is a scheme illustrating the synthesis of acyclic O-benzylated tetrahydroxamates 8a-c in an embodiment of the invention.

This example demonstrates the synthesis of acyclic O-benzylated tetrahydroxamates 8a-c (FIG. 8) in an embodiment of the invention.

The condensation reaction between 7a and 6a was performed as described above. Purification by flash chromatography using hexane/acetone (7/3) afforded 8a as a colorless oil (87%). $^1$H NMR (CDCl$_3$, 300 MHz, ppm): δ 1.29 (m, 6H), 1.61 (m, 12H), 2.36 (m, 8H), 2.47 (m, 2H), 3.60 (m, 6H), 4.77 (d, 21-1, J=5.7 Hz), 4.77 (s, 4H), 4.79 (s, 2H), 4.81 (s, 2H), 4.99 (m, 2H), 5.21 (m, 2H), 5.83 (m, 2H), 7.35 (m, 20H). $^{13}$C NMR (CDCl$_3$, 75 MHz, ppm): δ 24.3, 24.4, 26.7 (2), 26.9, 28.7, 31.0, 21.8, 32.3, 76.4, 76.8, 115.2, 118.4, 128.8 (2), 129.0 (2), 129.2, 129.3, 132.5, 134.7, 137.6, 174.7. ESI-MS: m/z=903.5 [M+H]$^+$; 925.5 [M+Na]$^+$.

The condensation reaction between 7b and 6b as described above afforded 8b as a colorless oil (83%). $^1$H NMR (CDCl$_3$, 300 MHz, ppm): (δ 1.29 (m, 12H), 1.60 (m, 14H), 2.05 (m, 2H), 2.37 (m, 4H), 3.60 (m, 6H), 4.23 (d, 2H, J=6.0 Hz), 4.78 (s, 6H), 4.82 (s, 2H), 4.97 (m, 2H), 5.22 (m, 2H), 5.80 (m, 2H), 7.36 (m, 20H). $^{13}$C NMR (CDCl$_3$, 75 MHz, ppm): δ 23.8, 24.4, 24.6, 26.7, 26.9, 29.1, 31.0, 31.8, 32.4, 33.4, 45.5, 76.3, 76.9, 115.2, 118.4, 128.8, 128.9, 129.0, 129.2 (2), 129.3, 132.5, 134.7, 138.3, 174.9. ESI-MS: m/z=959.5 [M+H]$^+$; 971.5 [M+Na]$^+$.

The condensation reaction between 7c and 6c as described above afforded 8c as a colorless oil (87%). $^1$H NMR (CDCl$_3$, 300 MHz, ppm): δ 1.28 (m, 18H), 1.38 (m, 2H), 1.59 (m, 14H), 2.06 (m, 2H), 2.37 (m, 8H), 3.60 (m, 6H), 4.24 (d, 2H, J=6.0 Hz), 4.79 (s, 6H), 4.83 (s, 2H), 4.94 (m, 2H), 5.22 (m, 2H), 5.84 (m, 2H), 7.37 (m, 20H). $^{13}$C NMR (CDCl$_3$, 75 MHz, ppm): δ 24.3, 24.6, 24.7, 26.8, 27.1, 28.8, 29.3, 29.4, 29.5, 32.4, 32.5, 33.7, 45.6, 76.4, 76.9, 114.6, 118.4, 128.8, 129.0 (2), 129.2, 129.3, 132.6, 134.8, 138.8, 175.1. ESI-MS: m/z=1015.5 [M+H]$^+$; 1037.5 [M+Na]$^+$.

Example 9

Figure 9:
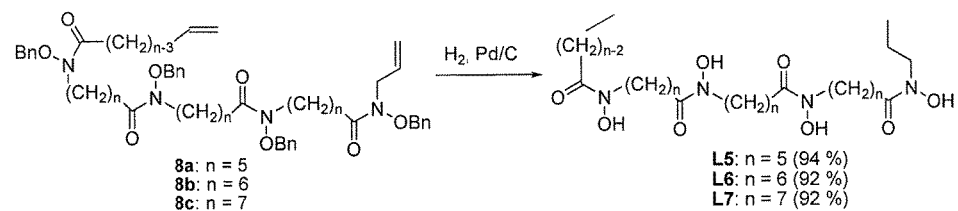
FIG. 9 is a scheme illustrating the synthesis of acyclic tetrahydroxamic acid chelators L5-7 in an embodiment of the invention.

This example demonstrates the synthesis of acyclic tetrahydroxamic acid chelators L5-7 (FIG. 9) in an embodiment of the invention.

Compound 8a (276 mg, 221 mol) was dissolved in MeOH (20 mL) and hydrogenated in a Paar apparatus at 30 psi H$_2$ in the presence of 10% Pd/C (20 mg) for 48 h. Pd/C was then removed by centrifugation at 8500 rpm. The supernatant was then centrifuged a second time and the solvent evaporated. The oily residue was dissolved in the minimum amount of MeOH, Et$_2$O was added until the solution became cloudy and placed in the fridge at 4° C. L5 precipitated as a white solid that was filtered and washed with Et$_2$O (187 mg, 94%). $^1$H NMR (DMSO, 300 MHz, ppm): δ 0.87 (m, 6H), 1.23 (m, 8H), 1.51 (m, 16H), 2.33 (m, 8H), 3.46 (m, 8H), 9.54 (s, 4H). $^{13}$C NMR (DMSO, 75 MHz, ppm): δ 11.1, 13.8, 21.9, 23.9, 25.9, 26.2, 31.4, 31.6, 47.0, 172.5. ESI-MS: m/z=547.3 [M+H]$^+$; 569.2 [M+Na]$^+$; 545.2 [M–H]$^-$; 581.2 [M+Cl]$^-$. Elemental analyses: Calculated for C$_{26}$H$_{50}$N$_4$O$_8$: C, 57.12; H, 9.22; N, 10.25%. Found: C, 56.14; H, 8.74; N, 9.85. Mp: 117° C.

Compound 8b was hydrogenated using the same procedure. A white precipitate formed. It was dissolved in hot isopropyl alcohol. Pd/C was then removed by centrifugation at 8500 rpm. The supernatant was centrifuged a second time and the solvent evaporated to form L6 as a white solid (92%). $^1$H NMR (DMSO, 300 MHz, ppm): δ 0.84 (m, 6H), 1.24 (m, 16H), 1.48 (m, 16H), 2.32 (m, 8H), 3.44 (m, 8H), 9.53 (s, 4H). $^{13}$C NMR (DMSO, 75 MHz, ppm): δ 11.1, 13.9, 19.6, 21.9, 23.9, 24.2, 26.0, 26.2, 28.5, 31.0, 31.6, 47.0, 172.6. ESI-MS: m/z=603.2 [M+H]$^+$; 625.3 [M+Na]$^+$; 601.3 [M–H]$^-$; 637.3 [M+Cl]$^-$. Elemental analyses: Calculated for C$_{30}$H$_{58}$N$_4$O$_8$: C, 59.77; H, 9.70; N, 9.29%. Found: C, 59.82; H, 9.43; N, 8.99. Mp: 139° C.

Compound 8c was hydrogenated using the same procedure. A white precipitate formed. It was dissolved in hot isopropyl alcohol. Pd/C was then removed by centrifugation at 8500 rpm. The supernatant was centrifuged a second time and the solvent evaporated to form L7 as a white solid (92%). $^1$H NMR (DMSO, 300 MHz, ppm): δ 0.83 (m, 6H), 1.24 (m, 24H), 1.47 (m, 16H), 2.31 (m, 8H), 3.45 (m, 8H), 9.54 (ms, 4H). $^{13}$C NMR (DMSO, 75 MHz, ppm): δ 11.1, 13.9, 19.6, 22.0, 24.2, 26.0, 26.3, 28.5, 28.6, 28.8, 31.1, 31.7, 47.0, 172.6. ESI-MS: m/z=659.4 [M+H]$^+$; 681.4 [M+Na]$^+$; 657.4[M–H]$^+$; 693.3 [M+Cl]$^-$. Elemental analyses: Calculated for C$_{34}$H$_{66}$N$_4$O$_8$: C, 61.98; H, 10.10; N, 8.50%. Found: C, 61.69; H, 9.79; N, 8.27. Mp: 122° C.

Example 10

Figure 10:
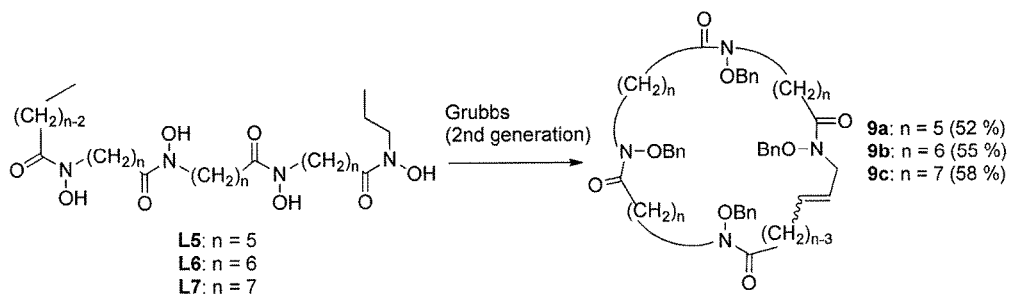
FIG. 10 is a scheme illustrating the synthesis of macrocyclic O-benzylated tetrahydroxamates 9a-c in an embodiment of the invention.

This example demonstrates the synthesis of macrocyclic O-benzylated tetrahydroxamates 9a-c (FIG. 10) in an embodiment of the invention.

Compound 8a (990 mg, 1.10 mmol) was dissolved in CH$_2$Cl$_2$ (1000 mL) and degassed by bubbling nitrogen in the solution for 20 minutes. Grubbs catalyst, 2$^{nd}$ generation (279 mg, 329 μmol) was then added and the mixture was refluxed for 15 h. The solvent volume was then reduced to ~200 mL in vacuo, cysteine (2.0 g, 16.5 mmol) and sodium hydroxide (2.63 g, 66 mmol) in water (100 mL) were added and the biphasic mixture was stirred for 20 h at 50° C. The organic layer was dried over MgSO$_4$, filtered and evaporated. The dark residue obtained was extracted with boiling hexane (3 times). Evaporation of the hexane afforded a lightly red oil which was purified by flash chromatography using hexane/acetone (7/3 followed by 6/4) to afford a golden oil of 9a as a 85/15 mixture of Z/E isomers (502 mg, 52%). $^1$H NMR (CDCl$_3$, 300 MHz, ppm): δ 1.25 (m, 6H), 1.57 (m, 12H), 2.32 (m, 8H), 2.42 (m, 2H), 3.58 (m, 6H), 4.10 (d, 1.7H, J=5.4 Hz), 4.24 (d, 0.3H, J=5.4), 4.75 (s, 6H), 4.77 (s, 2H), 5.47 (m, 1H), 5.65 (m, 1H), 7.34 (m, 20H). $^{13}$C NMR (CDCl$_3$, 75 MHz, ppm): δ 24.3, 24.4, 24.5, 26.4, 26.5, 26.8, 27.2, 31.8, 32.3, 45.1, 76.2, 76.3, 124.8, 128.7, 128.8, 128.9 (2), 129.3, 129.4, 174.8. ESI-MS: m/z=875.4 [M+H]$^+$; 697.3 [M+Na]$^+$.

Compound 8b was treated using the same procedure and afforded a colorless oil of 9b (55%) as a mixture of the Z/E isomers (92/8). $^1$H NMR (CDCl$_3$, 300 MHz, ppm): δ 1.25 (m, 12H), 1.57 (m, 12H), 1.67 (m, 2H), 2.03 (m, 2H), 2.31 (m, 8H), 3.59 (m, 6H), 4.12 (d, 1.85H, J=4.8 Hz), 4.23 (d, 0.15H, J=6.0 Hz), 4.73 (s, 2H), 4.76 (s, 6H), 5.47 (m, 1H), 5.58 (m, 1H), 7.35 (m, 20H). $^{13}$C NMR (CDCl$_3$, 75 MHz, ppm): δ 23.9, 24.4, 24.5, 26.4, 26.5, 26.8, 29.0, 29.3, 31.0, 31.6, 31.7, 32.3, 45.2, 124.7, 128.7, 128.7, 128.8, 129.2 (2), 134.2, 134.8, 174.8. ESI-MS: m/z=931.4 [M+H]$^+$; 953.4 [M+Na]$^+$.

Compound 8c was treated using the same procedure and afforded a colorless oil of 9c (58%) as a mixture of the Z/E isomers (88/12). $^1$H NMR (CDCl$_3$, 300 MHz, ppm): δ 1.26 (m, 18H), 1.37 (m, 2H), 2.04 (m, 2H), 2.34 (m, 8H), 3.59 (m, 6H), 4.13 (d, 1.76H, J=5.7 Hz), 4.23 (d, 0.24H, J=6.6 Hz), 4.77 (s, 6H), 4.79 (s, 2H), 5.46 (m, 1H), 5.60 (m, 1H), 7.36 (m, 20H). $^{13}$C NMR (CDCl$_3$, 75 MHz, ppm): δ 24.3, 24.6, 24.7, 26.6, 27.0, 28.7, 29.1 (2), 29.2, 29.3, 29.4, 29.8, 32.1, 32.3, 32.5, 45.5, 76.3, 124.3, 128.7, 128.8, 128.9, 129.0, 129.2, 129.3, 134.7, 134.9, 175.0. ESI-MS: m/z=988.4 [M+H]$^+$.

Example 11

Figure 11:
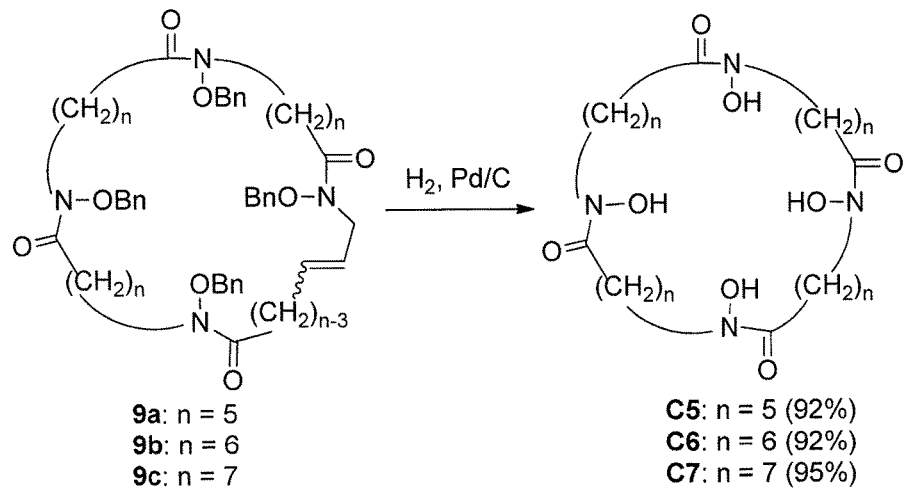
FIG. 11 is a scheme illustrating the synthesis of macrocyclic tetrahydroxamic acid chelators C5-7 in an embodiment of the invention.

This example demonstrates the synthesis of macrocyclic tetrahydroxamic acid chelators C5-7 (FIG. 11) in an embodiment of the invention.

Compound 9a (494 mg, 575 μmol) was dissolved in MeOH (50 mL) and hydrogenated in a Paar apparatus at 30 psi H$_2$ in the presence of 10% Pd/C (25 mg) for 48 h. Pd/C was removed by centrifugation at 8500 rpm. The supernatant was then centrifuged a second time and the solvent evaporated. The oily residue was dissolved in the minimum amount of MeOH, Et$_2$O was added until the solution became cloudy and placed in the fridge at 4° C. C5 precipitated as a white solid that was filtered and washed with Et$_2$O (268 mg, 92%). $^1$H NMR (DMSO, 300 MHz, ppm): δ 1.20 (m, 8H), 1.49 (m, 16H), 2.32 (m, 8H), 3.47 (t, 8H, J=6.6 Hz), 9.50 (s, 4H). $^{13}$C NMR (DMSO, 75 MHz, ppm): δ 23.9, 25.7, 26.1, 31.5, 46.8, 172.5. ESI-MS: m/z=517.2 [M+H]$^+$; 539.2 [M+Na]$^+$; 515.2 [M−H]$^-$. Elemental analyses: Calculated for C$_{24}$H$_{44}$N$_4$O$_8$: C, 55.80; H, 8.58; N, 10.84%. Found: C, 55.74; H, 8.80; N, 9.64. Mp: 150° C.

Compound 9b was hydrogenated using the same procedure. A white precipitate formed that was dissolved in hot isopropyl alcohol. The Pd/C was then removed by centrifugation at 8500 rpm. The supernatant was centrifuged a second time and the solvent evaporated to leave C6 as a white solid (92%). $^1$H NMR (DMSO, 300 MHz, ppm): δ 1.23 (m, 16H), 1.49 (m, 16H), 2.31 (t, 8H, J=7.2 Hz), 3.46 (t, 8H, J=6.6 Hz), 9.52 (s, 4H). $^{13}$C NMR (DMSO, 75 MHz, ppm): δ 24.2, 25.8, 26.1, 28.4, 31.6, 48.9, 172.6. ESI-MS: m/z=573.3 [M+H]$^+$; 595.3 [M+Na]$^+$; 571.3 [M−H]$^-$; 607.2 [M+Cl]$^-$. Elemental analyses: Calculated for C$_{28}$H$_{52}$N$_4$O$_8$: C, 58.72; H, 9.15; N, 9.78%. Found: C, 58.08; H, 8.93; N, 9.37. Mp: 167° C.

Compound 9c was hydrogenated using the same procedure. A white precipitate formed that was dissolved in hot isopropyl alcohol. The Pd/C was then removed by centrifugation at 8500 rpm. The supernatant was centrifuged a second time and the solvent evaporated to leave C7 as a white solid (95%). $^1$H NMR (DMSO, 300 MHz, ppm): δ 1.24 (m, 24H), 1.48 (m, 16H), 2.32 (t, 8H, J=7.2 Hz), 3.47 (t, 8H, J=6.6 Hz), 9.51 (s, 4H). $^{13}$C NMR (DMSO, 75 MHz, ppm): δ 24.2, 25.9, 26.2, 28.4, 28.7, 31.6, 46.8, 172.6. ESI-MS: m/z=629.3 [M+H]$^+$; 651.3 [M+Na]$^+$; 627.2 [M−H]$^-$; 663.2 [M+Cl]$^-$. Elemental analyses: Calculated for C$_{32}$H$_{60}$N$_4$O$_8$: C, 61.12; H, 9.62; N, 8.91%. Found: C, 60.96; H, 9.98; N, 8.60. Mp: 172° C.

Example 12

Figure 12A:
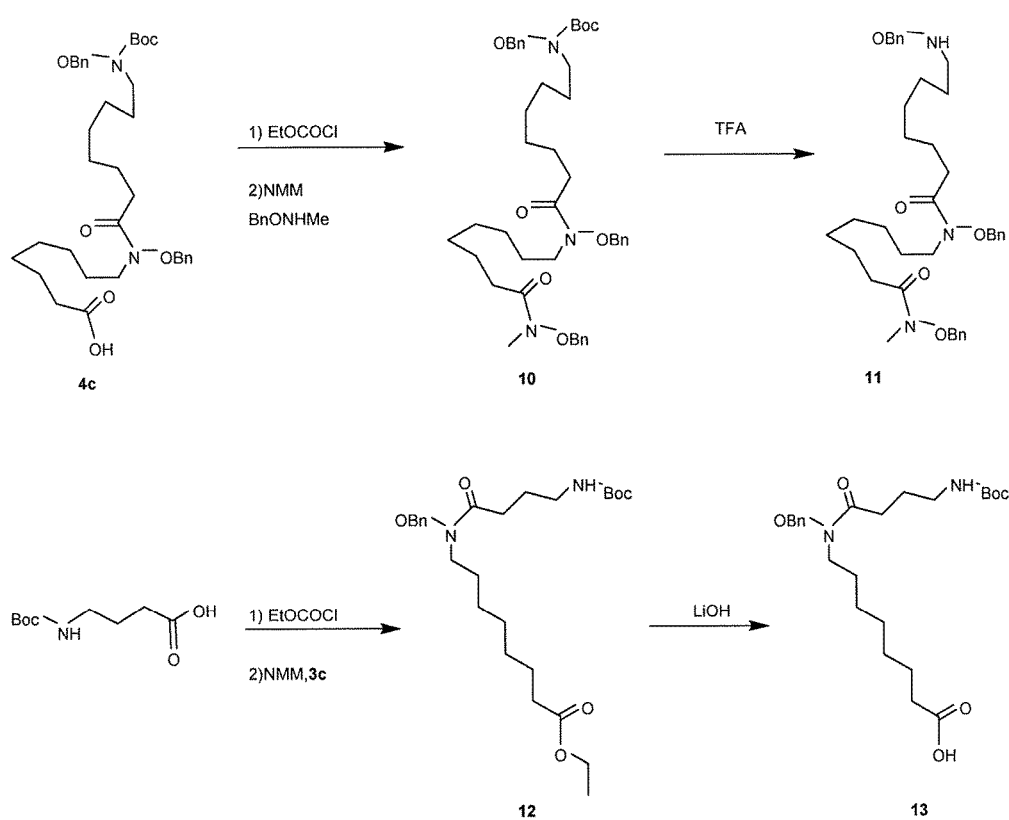
FIGS. 12A and 12B are schemes illustrating the synthesis of NCS-activated tetrahydroxamic acid 17 in an embodiment of the invention.
Figure 12B:
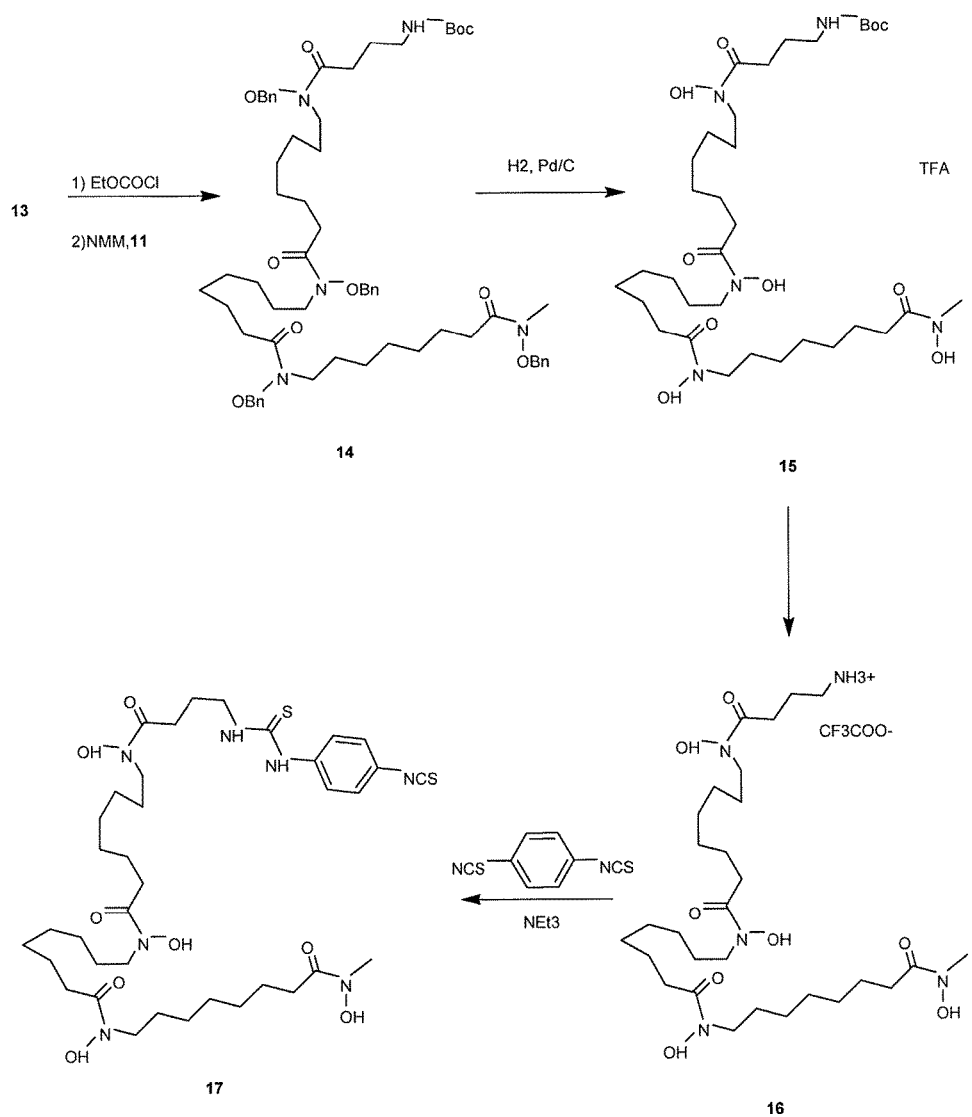

This example demonstrates the synthesis of NCS-activated tetrahydroxamic acid 17 (FIGS. 12A and 12B) in an embodiment of the invention.

To compound 4c (3.034 g, 4.95 mmol) in dry Et$_2$O (75 mL) cooled in an ice bath was added EtOCOCl (566 μL, 5.94 mmol) followed by NMM (817 μL, 7.43 mmol). The solution was stirred for 15 min at 0° C. and the white precipitate filtered. The filtrate was poured onto BnONHMe (849 mg, 6.19 mmol) and stirred overnight at RT. The solution was washed with 1N HCl and 1M Na$_2$CO$_3$ successively, dried over MgSO$_4$ and purified by silica gel chromatography using hexane/acetone (4:1) to afford 10 as a colorless oil (2.97 g, 82%). $^1$H NMR (CDCl$_3$, 300 MHz, ppm): δ 1.28 (m, 12H), 1.50 (s, 9H), 1.59 (m, 8H), 2.35 (m, 4H), 3.19 (s, 3H), 3.38 (t, 2H, J=7.2 Hz), 3.60 (t, 2H, J=6.9 Hz), 4.79 (s, 2H), 4.82 (s, 4H), 7.31-7.42 (m, 15H). ESI-MS: m/z=732.4 [M+H]$^+$; 754.4=[M+Na]$^+$; 632.4=[M-Boc+2H]$^+$.

To compound 10 (2.406 g, 3.29 mmol) dissolved in CH$_2$Cl$_2$ (10 mL), was added TFA (1.513 mL, 19.7 mmol). The solution was stirred overnight at RT, diluted to a volume of 50 mL of CH$_2$Cl$_2$ and 50 mL of water. Solid Na$_2$CO$_3$ was added until pH=10-11. The CH$_2$Cl$_2$ layer was dried over MgSO$_4$ and evaporated to afford 11 as a colorless oil (1.91 g, 92%). $^1$H NMR (CDCl$_3$, 300 MHz, ppm): δ 1.28 (m, 12H), 1.46 (m, 2H), 1.51-1.61 (m, 6H), 2.33-2.39 (m, 4H), 2.91 (t, 2H, J=6.9 Hz), 3.19 (s, 3H), 3.60 (t, 2H, J=6.9 Hz), 4.70 (s, 2H), 4.79 (s, 2H), 4.81 (s, 2H), 7.28-7.38 (m, 15H). ESI-MS: m/z=632.4 [M+H]$^+$; 654.3=[M+Na]$^+$.

To N-Boc-γ-aminobutyric acid (2.374 g, 11.7 mmol) in dry Et$_2$O (50 mL) cooled in an ice bath, was added EtOCOCl (1.337 mL, 14.04 mmol) followed by NMM (1.93 mL, 17.55 mmol). After stirring for 15 min at 0° C., the white precipitate was filtered, and the filtrated added to compound 3c and the solution was stirred overnight at RT. The solution was washed successively with 1N HCl and 1M Na$_2$CO$_3$, dried over MgSO$_4$ and purified by silica gel chromatography using hexane/acetone (85:15 to 75:25) to afford compound 12 as a colorless oil (4.76 g, 85%). $^1$H NMR (CDCl$_3$, 300 MHz, ppm): δ 1.25 (t, 3H, J=7.2 Hz), 1.43 (m, 6H), 1.62 (s, 9H), 1.73 (m, 4H), 1.75-1.82 (m, 2H), 2.27 (t, 2H, J=7.2 Hz), 2.42 (t, 2H, J=7.2 Hz), 3.10-3.16 (m, 2H), 3.62 (t, 2H, J=6.9 Hz), 4.12 (q, 2H, J=7.2 Hz), 4.71 (s, 1H, broad), 4.80 (s, 2H), 7.35-7.43 (m, 5H). $^{13}$C NMR (CDCl$_3$, 75 MHz, ppm): δ

14.4, 25.1, 26.8, 27.0, 28.6, 29.1, 29.2, 31.1, 34.5, 60.4, 76.5, 128.9, 129.2, 129.4, 156.2, 174.0. ESI-MS: m/z=479.3 [M+H]$^+$; 503.3=[M+Na]$^+$; 379.2=[M-Boc+2H]$^+$.

To compound 12 (4.745 g, 9.91 mmol) dissolved in THF (30 mL)+MeOH (10 mL), was added 2N LiOH (9.91 mL, 18.82 mmol) and the solution was stirred overnight at RT. After removal of volatiles in vacuum, Et$_2$O and 1N HCl was added to the residue. The organic layer was dried over MgSO$_4$ and evaporated to afford 13 as a white solid (4.20 g, 94%). Mp=50° C. $^1$H NMR (CDCl$_3$, 300 MHz, ppm): δ 1.31 (m, 6H), 1.43 (s, 9H), 1.62 (m, 4H), 1.73-1.82 (m, 2H), 2.32 (t, 2H, J=7.2 Hz), 2.42 (t, 2H, J=6.9 Hz), 3.12 (m, 2H), 3.62 (m, 2H), 4.74 (s, 1H, broad), 4.80 (s, 2H), 7.38 (m, 5H). $^{13}$C NMR (CDCl$_3$, 75 MHz, ppm): δ 24.8, 24.9, 26.6, 26.9, 28.6, 28.9, 29.0, 29.9, 34.1, 40.4, 66.1, 76.4, 128.9, 129.2, 129.4, 178.6. ESI-MS: m/z=451.3 [M+H]$^+$; 473.3=[M+Na]$^+$; 351.2=[M-Boc+2H]+.

To compound 13 (2.24 g, 4.95 mmol) in dry Et$_2$O (50 mL) cooled in an ice bath was added EtOCOCl (570 μL, 5.99 mmol) followed by NMM (823 μL, 7.49 mmol). The solution was stirred for 15 min at 0° C. and the white precipitate filtered. The filtrate was poured onto compound 14 (3.939 g, 6.23 mmol) and stirred overnight at RT. The solution was washed with 1N HCl and 1M Na$_2$CO$_3$ successively, dried over MgSO$_4$ and purified by silica gel chromatography using hexane/acetone (7:3 to 6:4) to afford 14 as a colorless oil (4.46 g, 85%). $^1$H NMR δ 1.28 (m, 18H), 1.43 (s, 9H), 1.59 (m, 12H), 1.74-1.81 (m, 2H), 2.30-2.44 (m, 8H), 3.09-3.16 (m, 2H), 3.19 (s, 3H), 3.60 (m, 6H), 4.72 (s, 1H, broad), 4.79 (s, 6H), 4.82 (s, 2H), 7.37 (m, 20H). $^{13}$C NMR (CDCl$_3$, 75 MHz, ppm): δ 24.6, 24.7, 24.8, 24.9, 26.8, 27.0, 27.1, 28.6, 29.3, 29.5, 29.9, 31.1, 32.6, 40.4, 69.9, 76.3, 76.4, 128.9 (2), 129.0, 129.1, 129.3, 129.4 (2), 134.9, 156.3. ESI-MS: m/z=1064.5 [M+11]$^+$; 1086.6=[M+Na]$^+$; 964.6=[M-Boc+2H]$^+$.

Compound 14 (888 mg, 834 μmol) dissolved in MeOH (25 mL) was placed under a 30 psi H$_2$ pressure in a Paar apparatus in the presence of 10% Pd/C for 48 h. Pd/C was then removed by centrifugation at 8500 rpm for 15 min. The supernatant was then centrifuged a second time and the solvent evaporated to form 15 as a white solid (525 mg, 91%). Mp=115° C. $^1$H NMR (DMSO-d$_6$, ppm): δ 1.24 (m, 18H), 1.37 (s, 9H), 1.50 (m, 12H), 1.60 (m, 2H), 2.32 (m, 8H), 2.88-2.94 (m, 2H), 3.07 (s, 3H), 3.46 (m, 6H). $^{13}$C NMR (DMSO-d$_6$, 75 MHz, ppm): δ 24.2, 26.1, 26.3, 26.7, 28.3, 28.6, 28.8, 29.2 31.5, 31.7, 47.0, 77.4, 155.6, 172.6, 172.9, 180.8. ESI-MS: m/z=704.4 [M+H]$^+$; 726.4=[M+Na]$^+$; 604.3=[M-Boc+2H]$^+$; 702.4 [M-H]$^-$; 738.4=[M+Cl]$^-$.

Compound 15 (415 mg, 590 μmol) was dissolved in TFA (5 mL) and stirred overnight at RT. TFA was evaporated in vacuum and the residue triturated in Et$_2$O until formation of a solid. The product was reprecipitated twice by dissolution in the minimum of MeOH and addition of Et$_2$O to yield a white solid (385 mg, 91%). Mp=68° C. $^1$H NMR (CD$_3$OD, ppm): δ 1.35 (m, 18H), 1.60 (m, 12H), 1.87-1.96 (m, 2H), 2.45 (m, 6H), 2.63 (t, 2H, J=7.2 Hz), 2.96 (t, 2H, J=7.2 Hz), 3.19 (s, 3H), 3.56-3.63 (m, 6H). $^{13}$C NMR (CD$_3$OD, 75 MHz, ppm): δ 23.8, 26.0, 27.6, 27.7, 27.8, 30.2, 30.5, 33.1, 33.4, 40.6, 49.0, 157.3, 174.3, 176.2. ESI-MS: m/z=604.3 [M+H]$^+$; 628.3=[M+Na]$^+$; 602.4 [M-H]$^-$; 638.4=[M+Cl]$^-$.

To compound 16 (158 mg, 220 μmol) dissolved in iso-propanol (20 mL)+water (2.4 mL) was added a solution of 1,4-phenylenediisothiocyanate (211 mg, 1.10 mmol) in chloroform (11 mL) immediately followed by triethylamine (92 L, 660 mol). After stirring overnight at RT, an ESI-MS analysis of the solution shows the complete formation of compound 17 and the absence of initial amine or dimeric product: m/z=796.3 [M+H]$^+$; 818.4=[M+Na]$^+$; 794.4 [M-H]$^-$; 830.4=[M+Cl]$^-$. Purification was performed by reverse phase HPLC.

Example 13

This example demonstrates a general procedure for the preparation of Zr$^{IV}$ complexes in an embodiment of the invention.

To zirconium(IV) acetylacetonate (81 mg, 162 μmol) dissolved in 10 mL dry methanol under nitrogen atmosphere was added ligand L7 (113 mg, 171 μmol) dissolved in 10 mL iso-propyl alcohol. The solution was heated for 14 h at 70° C., resulting in a milky solution with the complex partially precipitated. Analysis of the solution by ESI(+)-MS confirmed the formation of 1:1 (metal:ligand) complex: [M+H]$^+$=745.3 (+Zr isotopic distribution peaks). The solution was evaporated, resulting in a pale yellow powder. Residual zirconium(IV) acetylacetonate and ligand were removed by boiling and filtering the solid successively in methanol and iso-propyl alcohol. After drying in vacuum, 91 mg of pale yellow solid were obtained (76%). A sample was analyzed by ICP-OES for Zr content. % $Zr_{calc}$=12.23%, % $Zr_{found}$=13.29 (within the experimental error limits of the analysis which is 10%).

All complexes were prepared using the same procedure. Only L6, L7, and C7 formed a complex that could be detected by ESI(+)-MS. All complexes had a Zr content within the error range of the ICP-OES analysis method, except for Zr:L6.
Zr-C5, yield=92%, not detected in ESI(+)-MS. % $Zr_{calc}$=15.11. found=14.7.
Zr-L5, yield=94%, not detected in ESI(+)-MS. % $Zr_{calc}$=14.39. found=13.38.
Zr-C6, yield=82%, not detected in ESI(+)-MS. % $Zr_{calc}$=13.82. found=14.14.
Zr-L6, yield=96%, ESI(+)-MS [M+H]$^+$=689.2. % $Zr_{calc}$=13.22. found=15.11.
Zr-C7, yield=78%, ESI(+)-MS [M+H]$^+$=715.3. % $Zr_{calc}$=12.74. found=12.59.

Example 14

This example demonstrates $^{89}$Zr production in an embodiment of the invention.

$^{89}$Zr was produced and purified at the National Institutes of Health, Bethesda, Md., USA, by the following procedure: Pressed pellets of yttrium metal (200 mg, 99.99% purity; American Elements, USA) were irradiated with a proton beam of 15 MeV and a current of 20 μA for 2-4 h on a GE PETtrace cyclotron. $^{89}$Zr was separated from the yttrium target material by the use of hydroxamate resin as described by Holland et al. (*Nucl. Med. Biol.* 2009, 36, 729-739). Briefly, the target material was dissolved in 4×0.5 mL fraction of 6M HCl. After 1 h, the undissolved solid residue was separated by filtration, the resulting solution diluted to 5 mL with de-ionized water and loaded onto the hydroxamate resin column. The column was then washed with 4×2.5 mL of 2M HCl and 4×2.5 mL de-ionized water. After the solution was removed from the column, the $^{89}$Zr was eluted with successive portions of 1M oxalic acid. The first 0.4 mL fraction was discarded and the next 0.7 mL fraction collected for further use.

Example 15

This example demonstrates complexation of L5-7 and C5-7 with $^{89}$Zr in an embodiment of the invention.

All solutions described below were prepared with de-ionized water purified through a Chelex column prior to use. Stock solutions of $^{89}$Zr at pH 7 were prepared as follow: to 450 µL of the $^{89}$Zr solution in oxalic acid were added 450 µL of a 1M $Na_2CO_3$ solution and the pH was adjusted to 7 by addition of small aliquots of a 0.1 M $Na_2CO_3$ or 0.1 M HCl. 450 µL of water containing 3% bovine serum albumin were then added. To 45 µL of stock solution (~1.3 MBq of $^{89}$Zr in a typical experiment) were added 7.5 nmol (5 µL) of L5, L6, L7, C5, C6, or C7 in DMSO or the natural siderophore desferrioxamine B (DFB) mesylate in de-ionized water. These solutions were incubated at desired temperatures and time of reaction and analyzed by ITLC-SG using a 50 mM EDTA (ethylenediaminetetraacetic acid) solution adjusted to pH=7 in de-ionized water as eluant, and analyzed with a Typhoon 8600 scanner (GE Healthcare) in phosphorimaging mode. The percentage of the activity bound to the ligand after TLC was calculated by converting the TLC scan into a chromatogram and integrating the peak corresponding to the spot at the bottom of the TLC. Activity ratios were averaged out of a minimum of 2 TLCs for each condition. The influence of time and temperature on the complexation yield of $^{89}$Zr by L5, L6, L7, C5, C6 and C7 and DFB is shown in Table 1.

TABLE 1

| Ligand | 20° C. | | 50° C. | 80° C. |
|---|---|---|---|---|
| | 30 min | 120 min | 30 min | |
| L5 | 60% | 71% | 73% | 87.3% |
| C5 | 17% | 22% | 23% | 29% |
| L6 | 82% | 95% | 96% | >99% |
| C6 | 77% | 79% | 92% | 92% |
| L7 | 88% | >99% | >99% | >99% |
| C7 | 92% | >99% | >99% | >99% |
| DFB | >99% | >99% | >99% | >99% |

For the stability studies described below, higher activities were used with ~50 MBq $^{89}$Zr reacted with 38 nmol of ligand. The specific activity achieved was 0.96 MBq/nmol with L5, 0.30 MBq/nmol with C5, 1.26 MBq/nmol with L6, 1.21 MBq/nmol with C6, and 1.31 MBq/nmol with L7, C7, and DFB.

Example 16

This example demonstrates in vitro stability of the [$^{89}$Zr]-zirconium(IV) complexes in an embodiment of the invention.

10 µL of each $^{89}$Zr complex solution prepared as described above in Example 14 were incubated for 7 days in 40 µL Phosphate-Buffered Saline (PBS) (pH 7.4-10% DMSO) at 20° C., 40 µL sodium phosphate buffer (0.1 M, pH 6.5-10% DMSO) at 37° C., 40 µL human serum at 37° C., or 40 µL 50 mM EDTA (pH 7, 10% DMSO) at 37° C., respectively, and analyzed using the chromatographic system described in the above section after 1 h, 3 h, 1, 2, 3, 4, 5, 6, and 7 days.

Figure 13:
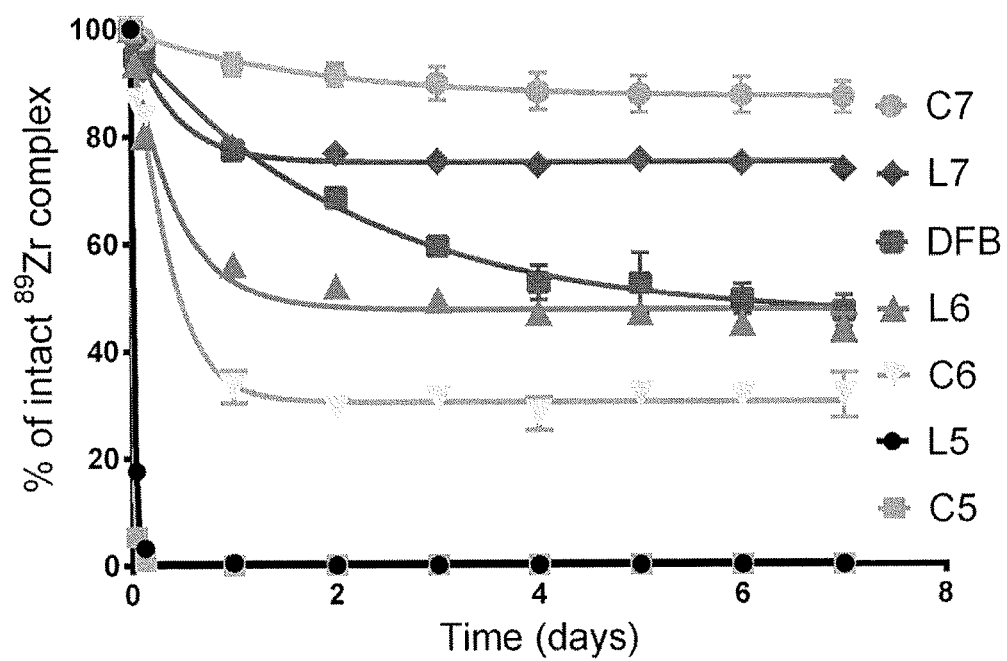
FIG. 13 is a graph illustrating the stability of the $^{89}$Zr-complexes in 50 mM EDTA at pH 7 and 37° C. over 7 days (n=4).

Stability of the $^{89}$Zr-complexes in 0.1 M sodium phosphate buffer at pH 6.5 over 7 days is shown in Table 2. In addition, stability of the $^{89}$Zr-complexes in 50 mM EDTA at pH 7 and 37° C. over 7 days (n=4) is shown in FIG. 13.

TABLE 2

| | Fraction of intact complex | | |
|---|---|---|---|
| Ligand | 1 Day | 4 Days | 7 Days |
| L5 | 93% | 89% | 77% |
| C5 | 69% | 46% | 42% |
| L6 | 97% | 94% | 94% |
| C6 | 89% | 79% | 61% |
| L7 | 99% | 98% | 98% |
| C7 | >99% | 99% | 99% |
| DFB | 99% | 98% | 98% |

Example 17

This example demonstrates a quantum chemical study of the [$^{89}$Zr]-zirconium(IV) complexes in an embodiment of the invention.

The X-ray structure of $Pu^{IV}$ complexed with DFE reported previously (Neu et al., Angew. Chem. Int. Ed. 2000, 39, 1442-1444) was used as a template to build the $Zr^{IV}$-C7 complex. After the Zr substitution for Pu, each amide group in the ring was converted to (—$CH_2CH_2$—) and then a fourth hydroxamate group with a 9-carbon alkyl chain on each end was inserted. After the geometry optimization at the level of B3LYP/LanL2DZ, a $CH_2CH_2$ moiety in each ring were deleted, and the resulting $Zr^{IV}$-C7 complex was further optimized in the gaseous phase at the level of M06L with the pseudopotential LanL2DZ for the Zr atom and the 6-31+G* basis set for the rest of the atoms. The acyclic $Zr^{IV}$-L7 complex was constructed by modifying the optimized $Zr^{IV}$-C7 complex, and then energy minimized. Starting with these two structures, the rest of the cyclic and acyclic complexes were built successively by deleting a $CH_2$ moiety in each ring in their respective geometry optimized complex. To calculate the ΔG and ΔH for complexation reaction, each ligand was constructed from its corresponding geometry optimized complex by deleting $Zr^{IV}$, and then protonating each of the 4 hydroxamates. The geometries of these ligands were optimized at the level of M06L/6-31+G*. In order to approximate the solvent effect onto the energetics, single point energy calculations were also done in the reaction field of $H_2O$ with the PCM model as implemented in Gausssian 09 software (Frisch et al., Gaussian 09, revision A.02, Gaussian Inc., Wallingford Conn., 2009.) All calculations have utilized the 5-component d functions, and the coordinates of the ligands and complexes are listed in the supporting information.

The calculated ΔGs in the reaction field of water (Table 3) are all in good agreement with the relative stabilities of the $^{89}$Zr complexes observed in FIG. 13. It is also noted that all cyclic and acyclic complex formations are both enthalpy and entropy driven.

TABLE 3

| Ligand | ΔG | ΔH | TΔS |
|---|---|---|---|
| C7 | −66.4 (−71.0) | −42.3 (−45.2) | 24.1 (25.8) |
| L7 | −67.4 (−70.6) | −43.7 (−47.3) | 23.7 (23.3) |
| C6 | −60.0 (−62.2) | −37.1 (−36.7) | 22.9 (25.5) |
| L6 | −66.4 (−68.0) | −43.3 (−44.9) | 23.1 (23.1) |
| C5 | −44.7 (−49.2) | −22.4 (−23.8) | 22.3 (25.4) |
| L5 | −47.5 (−53.2) | −24.1 (−28.9) | 23.4 (24.3) |

For example, Zr-C7 is respectively 8.8 kcal/mol and 21.8 kcal/mol more stable than Zr-C6 and Zr-05 in terms of ΔG calculated in the reaction field of water. This energy difference correlates well with the observation that 87±3% of $^{89}$Zr remains complexed to C7 after a week while only 32±4% is still complexed to C6, and nearly none by C5. In terms of kinetics, the release of ~50% of $^{89}$Zr from C5 and C6 occurred within the first minutes and a single day, respectively. This suggests that $Zr^{IV}$ complexes exhibiting better thermodynamic stabilities also have higher energy barriers for the $Zr^{IV}$ release. The stability differences among the three cyclic complexes are primarily due to a ring strain, as manifested by their ΔH values since the entropy contribution at 298.15 K for the three complexes are all comparable (~23 to 26 kcal/mol). The calculated ring strain energy going from C7 to C6 is 8.8 kcal/mol, and further increases to 13.0 kcal/mol when going from C6 to C5, suggesting that reduction of the macrocycle cavity is detrimental to the stability of the resulting $Zr^{IV}$ complex.

The observed stability with the acyclic complexes also correlates well with their calculated ΔGs. A notable difference is that the ring strain energy going from L7 to L6 is only 2.6 kcal/mol as compared to the C7 to C6 transition being 8.8 kcal/mol. While a ring opening alleviates the ring strain of the L6 complex, it does not overcome the ring strain in L5 (14.8 kcal/mol for the L6 to L5 transition).

As to the relative stability of Zr-C7 over Zr-L7 observed after a week, the calculated ΔG difference between the two is only 0.4 kcal/mol, suggesting this stability difference rather to be related to kinetics. Without being bound to any theory or mechanism, it is believed that the two open alkyl chains in Zr-L7 fluctuate more than the alkyl chains in the more rigid Zr-C7. This fluctuation likely leads to a weakening of the Zr—O bonds, resulting in a lower energy barrier for the $Zr^{IV}$ release from L7. On the other hand, since the L6 complex is more stable than the C6 analogue by 5.8 kcal/mol, the observed higher stability of Zr-L6 over Zr-C6 can be attributed to thermodynamics. Whereas better thermodynamic stability does not necessarily achieve higher kinetic inertness, the present thermochemical calculations indicate that such a correlation exists in the smaller cyclic and acyclic ligands complexed with $Zr^{IV}$ studied here. On the other hand, when similar thermodynamic stabilities are achieved with L7 and C7, a beneficial macrocyclic effect on the kinetic inertness of C7 was observed.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of formula (I) or (II)

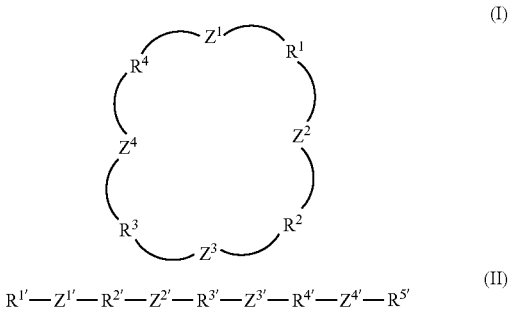

wherein
$Z^1$-$Z^4$ and $Z^{1'}$-$Z^{4'}$ are the same or different and each is

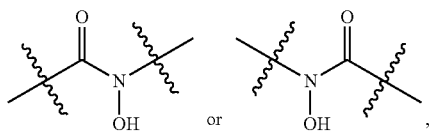 [SMILES: *C(=O)N(*)O ; *C(=O)N(*)O]

$R^1$, $R^2$, $R^3$, $R^4$, $R^{2'}$, $R^{3'}$, and $R^{4'}$, are the same or different and each is —$(CR^6R^7)_n$— or —$(CR^8R^9)_m$—X—$(CR^{10}R^{11})_m$—, $R^{1'}$ is —$(CR^6R^7)_n R^{12}$ or —$(CR^8R^9)_m$—X—$(CR^{10}R^{11})_m$—$R^{12}$, $R^{5'}$, $R^6$, $R^7$, $R^8$, $R^9$, $R^{10}$, $R^{11}$, and $R^{12}$ are the same or different and each is selected from hydrogen, alkyl, alkenyl, cycloalkyl, alkoxy, aryl, aryloxy, heteroaryl, hydroxyalkyl, thioalkyl, thioalkoxy, thioaryl, and an amino acid-containing group, wherein each group other than hydrogen is optionally substituted, X is O, S, or $NR^{13}$, $R^{13}$ is hydrogen, alkyl, alkenyl, cycloalkyl, aryl, or amino-acid containing group, wherein each group other than hydrogen is optionally substituted, n is an integer selected from 5-7, and m and m' are the same or different and each is an integer selected from 0-6, such that 4≤(m+m')≤6; and
wherein the compound optionally further comprises a biomolecule
(i) that is covalently linked, either directly or through a linker in the compound of formula (I), to a carbon or nitrogen atom of one or more of $R^1$-$R^4$, or
(ii) that is covalently linked, either directly or through a linker in the compound of formula (II), to carbon or nitrogen atom of one or more of $R^{1'}$-$R^{5'}$ or a nitrogen atom of one or both of $Z^{1'}$ or $Z^{4'}$.

2. The compound of claim 1, wherein each of $Z^1$, $Z^2$, $Z^3$, and $Z^4$ or each of $Z^{1'}$, $Z^{2'}$, $Z^{3'}$, and $Z^{4'}$ is

[structure]

3. The compound of claim 1, wherein
(i) each of $R^1$, $R^2$, $R^3$, and $R^4$ is —$(CR^6R^7)_n$—, or
(ii) each of $R^{2'}$, $R^{3'}$, and $R^{4'}$ is —$(CR^6R^7)_n$—, and $R^{1'}$ is —$(CR^6R^7)_n R^{12}$.

4. The compound of claim 3, wherein $R^6$ and $R^7$ are each hydrogen.

5. The compound of claim 1, wherein at least one of $R^1$, $R^2$, $R^3$, and $R^4$ or at least one of $R^{2'}$, $R^{3'}$, and $R^{4'}$ is —$(CR^8R^9)_m$—X—$(CR^{10}R^{11})_m$—.

6. The compound of claim 5, wherein $R^8$, $R^9$, $R^{10}$, and $R^{11}$ are each hydrogen.

7. The compound of claim 5, wherein m and m' are each 3.

8. The compound of claim 5, wherein X is O.

9. The compound of claim 1, wherein in the compound of formula (II), $R^{5'}$ is alkyl.

10. The compound of claim 1, wherein at least one of $R^{5'}$, $R^6$, $R^7$, $R^8$, $R^9$, $R^{10}$, $R^{11}$ and $R^{12}$ is not hydrogen.

11. The compound of claim 10, wherein at least one of $R^{5'}$, $R^6$, $R^7$, $R^8$, $R^9$, $R^{10}$, $R^{11}$ and $R^{12}$ is a substituted moiety selected from alkyl, alkenyl, cycloalkyl, alkoxy, aryl, aryloxy, heteroaryl, hydroxyalkyl, thioalkyl, thioalkoxy, thioaryl, and an amino acid-containing group.

12. The compound of claim 11, wherein the substituted moiety comprises at least substituent selected from halo, alkyl, alkenyl, alkynyl, hydroxy, nitro, amino, alkylamino, azido, epoxydyl, vinyl sulfonyl, thiocyano, isothiocyano, alkoxy, aryloxy, aralkoxy, carboxyl, carboxyalkyl, carboxyalkyloxy, amido, alkylamido, haloalkylamido, cyclooctenyl, pyridinyl, 1,4-dihydropyridazinyl, tetrazinyl, imidazolyl, and norbornenyl.

13. The compound of claim 12, wherein the compound further comprises a biomolecule
(i) that is covalently linked, either directly or through a linker in the compound of formula (I), to a carbon or nitrogen atom of one or more of $R^1$-$R^4$, or
(ii) that is covalently linked, either directly or through a linker in the compound of formula (II), to carbon or nitrogen atom of one or more of $R^{1'}$-$R^{5'}$ or a nitrogen atom of one or both of $Z^{1'}$ or $Z^{4'}$.

14. The compound of claim 13, wherein the biomolecule is a hormone, an amino acid, a peptide, a peptidomimetic, a protein, deoxyribonucleic acid (DNA), ribonucleic acid (RNA), a lipid, albumin, an antibody, an antibody fragment, an engineered antibody fragment, a receptor molecule, a receptor binding molecule, a hapten, a pre-targeting hapten, an aptamer, a nucleotide, an oligonucleotide, a polysaccharide, a bacteria, or a virus.

15. The compound of claim 1 selected from

[structures]

wherein each n is the same or different and is an integer from 5-7.

16. A complex comprising
(i) a compound of claim 1, and
(ii) $^{89}$Zr or $^{90}$Nb,
wherein the hydrogen on the hydroxy group of each of $Z^1$-$Z^4$ and $Z^{1'}$-$Z^{4'}$ is absent, so that both oxygens of $Z^1$-$Z^4$ and $Z^{1'}$-$Z^{4'}$ are chelated to $^{89}$Zr or $^{90}$Nb.

17. A composition comprising (a) the complex of claim 16; and (b) a carrier.

18. A method for positron emission tomography (PET) imaging of a subject, which method comprises:
(i) administering to the subject the complex of claim 16 in an amount effective to provide an image; and
(ii) exposing the subject to an energy source, whereupon a PET image of the subject is obtained.

19. A method of obtaining a positron emission tomography (PET) image of a tissue comprising exposing the tissue to the complex of claim 16 in an amount effective to provide an image, and exposing the tissue to an energy source, whereupon a PET image of the tissue is obtained.

20. The method of claim 19, wherein the tissue is from an organ, a tumor, lesion, carcinoma, sarcoma, or fibroid.

* * * * *